(12) United States Patent
Aman et al.

(10) Patent No.: US 7,999,001 B2
(45) Date of Patent: Aug. 16, 2011

(54) ANTIVIRAL COMPOUNDS AND METHODS OF USING THEREOF

(75) Inventors: Mohammad Javad Aman, Gaithersburg, MD (US); Sina Bavari, Frederick, MD (US); James C. Burnett, Richmond, VA (US); Kelly Lyn Warfield, Adamstown, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 669 days.

(21) Appl. No.: 12/013,640

(22) Filed: Jan. 14, 2008

(65) Prior Publication Data

US 2009/0012107 A1    Jan. 8, 2009

Related U.S. Application Data

(60) Provisional application No. 60/884,928, filed on Jan. 15, 2007.

(51) Int. Cl.
*A01N 43/12* (2006.01)
*A61K 31/38* (2006.01)
*C07D 333/00* (2006.01)
*C07D 495/00* (2006.01)

(52) U.S. Cl. .......................... 514/443; 549/43
(58) Field of Classification Search .................. 514/443; 549/43

See application file for complete search history.

(56) References Cited

OTHER PUBLICATIONS

Givens et al. "Detecton of Inhibition of Bovine Viral Diarrhea Virus by Aromatic Cationic Molecules" Antimicrobial Agents and Chemotherapy, Jul. 2003, pp. 2223-2230.*
Anne, J. et al. (1980) "Antifungal and Antibacterial Activities of Diarylamidine Derivatives" Antimicrobial Agents & Chemotherapy 18(2):231-239.
De. Clercq et al. (1980) "Diaryl Amidine Derivatives as Oncornaviral DNA Polymerase Inhibitors" J. Med. Chem. 23:787-795.
Tidwell et al. (1978) "Diarylamidine Derivatives with One or Both of the Aryl Moieties Consisting of an Indole or Indole-like Ring, Inhibitors of Arginine-Specific Esteroproteases" J. Med. Chem. 21(7):613-623.
Declercq, E. "Diaryl Amidine Derivatives as Oncornaviral DNA Polymerase Inhibitors", J. Med. Chem. 1980, vol. 23, pp. 787-795.
International Search Report and Written Opinion of the International Searching Authority, or the Declaration, mailed Sep. 11, 2008 received in PCT/US08/50975.

* cited by examiner

*Primary Examiner* — Sreeni Padmanabhan
*Assistant Examiner* — Kendra D Carter
(74) *Attorney, Agent, or Firm* — Elizabeth Arwine

(57) ABSTRACT

Disclosed herein are compounds which exhibit antiviral activity against a plurality of viruses belonging to different families such as Bornaviridae, Filoviridae, Paramyxoviridae, Rhabdoviridae, Arenaviridae, Bunyaviridae, Orthomyxoviridae, and Poxviridae. Thus, methods of preventing, inhibiting, or reducing the viral activity of various viruses are provided as well as methods of treating viral infections.

10 Claims, 13 Drawing Sheets

NSC 236723
2-(2-(5-(amino(imino)methyl)-1-benzofuran-2-yl)vinyl)-1H-benzimidazole-5-carboximidamide NSC 249202
2-[(E)-2-(5-carbamimidoylbenzofuran-2-yl)ethenyl]benzofuran-6-carboximidamide NSC 128981
N-(3-((4-chlorophenyl)thio)-1,4-dioxo-1,4-dihydro-2-naphthalenyl)acetamide

Lassa Virus

ANTIVIRAL COMPOUNDS AND METHODS OF USING THEREOF

CROSS-REFERENCE TO RELATED APPLICATIONS

This application claims the benefit of U.S. Provisional Patent Application Ser. No. 60/884,928, filed 15 Jan. 2007, which is herein incorporated by reference.

ACKNOWLEDGEMENT OF GOVERNMENT SUPPORT

This invention was made by the United States Army Medical Research and Materiel Command, which is an agency of the United States Government. The Government has certain rights in this invention.

BACKGROUND OF THE INVENTION

1. Field of the Invention

The present invention generally relates to antiviral compounds and methods of using thereof.

2. Description of the Related Art

Negative strand RNA viruses (Baltimore classification system) include viruses belonging to the Bornaviridae, Filoviridae, Paramyxoviridae, Rhabdoviridae, Arenaviridae, Bunyaviridae, and Orthomyxoviridae families as well as other unassigned genera. Negative sense RNA viruses include some of the most pathogenic viruses known to human kind, such as the Ebola viruses, Marburg virus, Rift Valley Fever virus, Lassa virus, and Influenzavirus A.

The Ebola viruses, and the genetically-related Marburg virus, are filoviruses associated with outbreaks of highly lethal hemorrhagic fever in humans and primates in North America, Europe, and Africa. The Rift Valley Fever virus, which can cause hemorrhagic fever, killed about 400 people in Kenya in 1998 and thousands in Egypt in 1977 to 1978. The Lassa virus also causes hemorrhagic fever and causes about 5,000 deaths per year. Various strains of Influenzavirus A are known to case various flu epidemics which have killed thousands of people and the subtype H5N1 is considered as a potential pandemic threat.

Infections by viruses which cause viral hemorrhagic fever usually exhibit initial flu-like symptoms such as fever, vomiting, diarrhea and malaise. Consequently, before a deadly epidemic is suspected and the causative agent is identified, the initial patient(s) are misdiagnosed.

SUMMARY OF THE INVENTION

The present invention provides methods of preventing, inhibiting, or reducing the viral activity of a virus on or in a cell or a subject or treating an infection in a cell or a subject caused by a virus which comprises administering to the cell or the subject an effective amount of a compound having a structural formula selected from the group consisting of n is 1 or 2;

X$^1$, X$^2$, X$^3$, X$^4$, X$^5$ and X$^6$ are each independently C, N, S, O, SO$_2$, CR$^7$ or NR$^8$;

L is a linker which may be a direct bond or

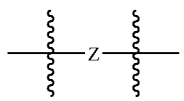

where Z is an optionally substituted alkyl, alkenyl, dialkenyl, trialkenyl, aryl, amide;

R$^1$, R$^2$, R$^3$, R$^4$, R$^5$, R$^6$ and R$^7$ are each independently hydrogen, amino, amine (e.g. nitrogen) with stabilized carbocations, carboxyl, optionally substituted alkyl, alkenyl, alkynyl, cycloalkyl, heterocycloalkyl, aryl, heteroaryl, alkoxy, aryoxy, cycloalkoxy, heteroaryloxy, alkoxycarbonyl, alkylamino, carbamoyl, alkylaminocarbonyl, alkylsulfhydryl, alkylhydroxymate, or an amide possessing alkyl substituent(s);

R$^8$ is hydrogen, OH, a halogen, or an optionally substituted alkyl; and

R$^9$ and R$^{10}$ are each independently optionally substituted mercapto alkyl, alkenyl, alkynyl, cycloalkyl, heterocycloalkyl, aryl, heteroaryl, alkoxy, aryoxy, cycloalkoxy, heteroaryloxy, alkoxycarbonyl, alkylamino, carbamoyl, alkylaminocarbonyl, alkylsulfhydryl, or alkylhydroxymate.

In some embodiments, at least one of X$^1$ or X$^2$ is N, S, O, SO$_2$, or NR$^8$. In some embodiments, the compound is Structural Formula A

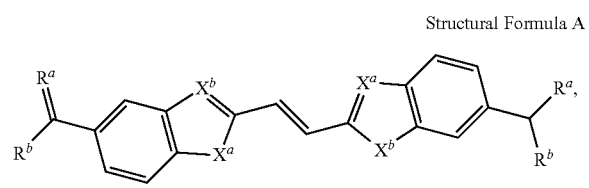

Structural Formula B

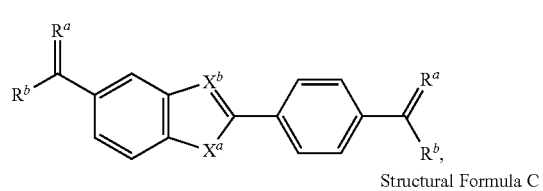

Structural Formula C

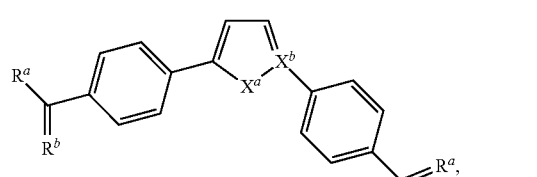

Structural Formula D

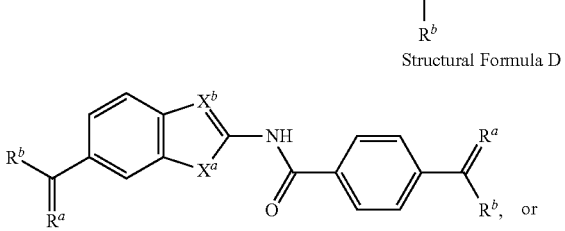

or

Structural Formula E

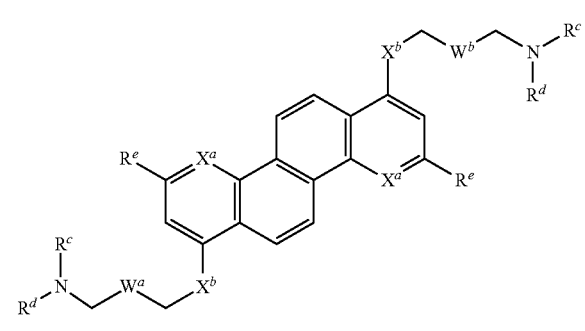

wherein

X$^a$ and X$^b$ are each independently C, N, NH, S, O, or CH;

W$^a$ and W$^b$ are each independently alkyl, alkenyl, alkynyl, cycloalkyl, heterocycloalkyl, or aryl;

R$^a$ and R$^b$ are each independently N, NH, O, OH, an oxime, an alkyloxime, an alkyl or a fused ring system such that R$^a$—CH$_2$—CH$_2$—R$^b$ form an imidazole ring; and R$^c$ and R$^d$ are each independently alkyl, alkenyl, alkynyl, cycloalkyl, heterocycloalkyl, aryl, heteroaryl, alkoxy, aryoxy, cycloalkoxy, heteroaryloxy, alkoxycarbonyl, alkylamino, carbamoyl, alkylaminocarbonyl, alkylsulfhydryl, or part of fused ring systems such that R$^c$ and R$^d$ form a cycloalkyl or heterocycloalkyl ring. In some embodiments, the compound is NSC 240890, NSC 240891, NSC 240893, NSC 240894, NSC 240895, NSC 240898, NSC 240899, NSC 266472, NSC 240900, NSC 278995, NSC 278997, NSC 278999, NSC 290107, NSC 290108, NSC 290111, NSC 291103, NSC 294199, NSC 294202, NSC 294206, NSC 294208, NSC 300509, NSC 300510, NSC 300511, NSC 308569, NSC 308570, NSC 308571, NSC 308572, NSC 308573, NSC 330688, NSC 330689, NSC 341909, NSC 341911, NSC 352341, NSC 369723, NSC 607617, NSC 23767, NSC 95397, NSC 128981, NSC 240899, NSC 264136, NSC 291103, NSC 369715 or NSC 306365. In some embodiments, the virus is a negative strand RNA virus or a double stranded DNA virus. In some embodiments, the virus belongs to a family selected from the group consisting of Bornaviridae, Filoviridae, Paramyxoviridae, Rhabdoviridae, Arenaviridae, Bunyaviridae, Orthomyxoviridae, and Poxyiridae. In some embodiments, the virus is an Ebolavirus, a Marburgvirus, an Arenavirus, an Influenzavirus, and an Orthopoxvirus. In some embodiments, the virus is Zaire Ebolavirus, Reston Ebolavirus, Sudan Ebolavirus, Ivory Coast Ebolavirus, Bundibugyo Ebolavirus, Marburgvirus, Lassa virus, Influenzavirus A, Cowpox virus, or Monkeypox virus. In some embodiments, the virus is not a reverse transcribing diploid single-stranded RNA virus or a reverse transcribing circular double-stranded DNA virus. In some embodiments, if the virus is an oncornavirus, the compound is an excluded compound.

In some embodiments, the present invention provides compounds having a structural formula falling within one of the general structural formulas described herein and compositions thereof. The compositions may have one or more compounds of the present invention. The compositions may further comprise pharmaceutically acceptable carriers, supplementary active compounds, and the like as disclosed herein.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description, serve to explain the principles of the invention.

DESCRIPTION OF THE DRAWINGS

This invention is further understood by reference to the drawings wherein:

FIG. 5D shows that NSC 306365 at 4 µM and 2 µM inhibit the replication of Lassa virus (Josiah strain) in Vero-E6 cells.

FIG. 6 shows NSC 369723 and NSC 294202 provided 100% protection and 90% of the control mice died from infection.

FIG. 7 shows the post-exposure dose-response efficacy of NSC 306365.

FIG. 11 shows that NSC 306365 prolongs the mean time to death in mouse model of Cowpox virus.

DETAILED DESCRIPTION OF THE INVENTION

The present invention relates to compounds and a pharmacophore model for compounds which exhibit antiviral activity. As used herein, "antiviral activity" refers to the activity of an agent that prevents, inhibits, or reduces the viral activity of a virus or the activity of a compound which destroys a virus. As used herein, "viral activity" refers to the ability of a virus to replicate, multiply, reproduce or infect a cell or a subject.

1. High Throughput Screening (HTS) Assays

For high throughput screening assays, a recombinant Ebola Zaire virus expressing green fluorescence protein (EBOV-GFP) was used. See Towner et al. (2005) *Virology* 332(1):20-27, which is herein incorporated by reference. Productive infection of cells with EBOV-GFP results in the cells emitting green fluorescent light when excited at 488 nm. In initial studies, the number of cells and multiplicity of infection (MOI) for EBOV-GFP and Vero-E6 cells to be used were optimized. Specifically, all possible combinations of different number of cells (about 10000 to about 50000 cells per well) and different MOIs (01, 1, 5, and 20) were tested in 24 well plates. 48 hours after infection cells were fixed in formalin and the percent infection (% GFP positive cells) was determined to identify standard conditions that results in about 50 to about 70% infection.

Then the assay format was adopted to a 96 well format and the MOI was adjusted to achieve about 50 to about 70% infection within about 48 hours. Specifically, cell numbers were adjusted based on the surface area of a well of 96 well plate and the respective MOI was calculated and examined using methods known in the art.

To screen a plurality of compounds, Vero E6 cells ($5 \times 10^4$ cells/well) were grown to monolayers in 96 well plates to which 20 µM of each compound was added to a given well. Subsequently (within about 1 to 2 hours), EBOV-GFP $5 \times 10^4$ pfu was added to the cells and then the cells were incubated at 37° C. for 48 hours. Then the cells were fixed for 3 days in formalin, the nuclei were stained with Hoechst Dye. To quantify the percent infection and the intensity of green fluorescent light from GFP expression, a Discovery-1 high content screening device (Molecular Devices Corp., Downingtown, Pa.) was applied for 9 regions per well. Percent infection in the treated cells was compared with untreated cells (controls) on the same 96 well plates.

Figure 1:
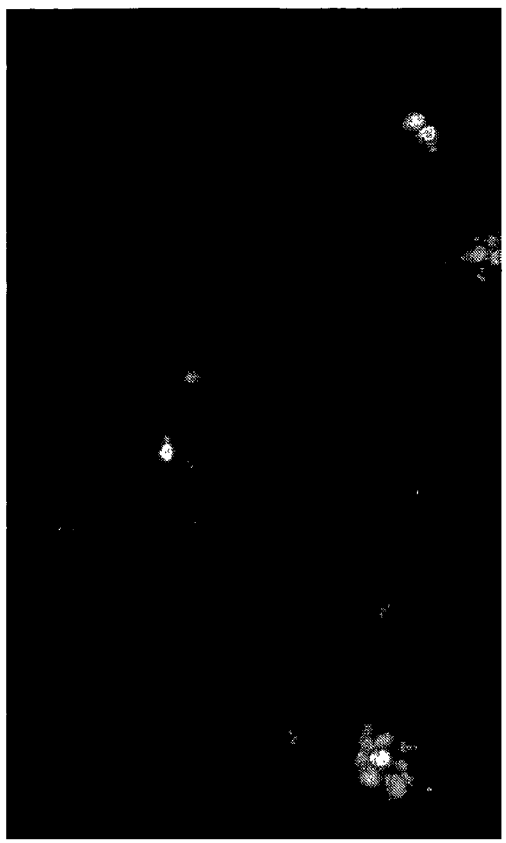
FIG. 1 shows cells emitting green fluorescent light (light spots) in the control sample (left panel) and a sample treated with a compound.
Figure 1:
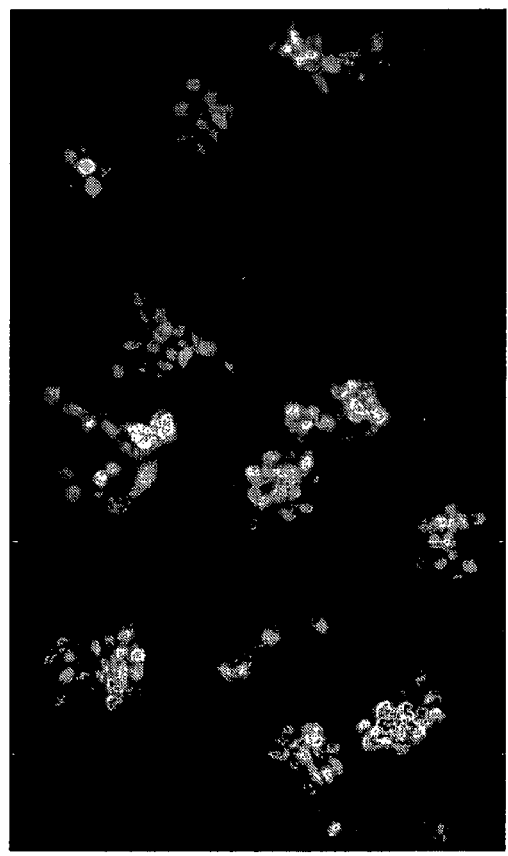

About 2400 compounds from National Cancer Institute's open repository were screened in duplicate at 20 µM each. FIG. 1 is an image showing cells emitting green fluorescent light (light spots) in the control sample (left panel) and a sample treated with a compound. The percent infection in control wells were set as 100% and percent inhibition by the compounds (average of the duplicate) was calculated relative to the control wells. Compounds that inhibited infection by at least about 30% were considered hits. Hits were reexamined twice in a secondary screen using the same assay in triplicate and only those compounds that consistently inhibited EBOV infection were selected for further analysis. The secondary screen resulted in 36 compounds for further analysis. The NCI identifiers (NSC numbers) and the % inhibition observed for the 36 compounds at 20 µM are summarized in Table 1.

TABLE 1

| Compound | NSC Number* | EBOV % Inhibition (20 μM) | Monkey Pox % Inhibition (20 μM) |
|---|---|---|---|
| 2-(4-carbamimidoylphenyl)benzothiophene-6-carboximidamide; 2-hydroxypropanoic acid | 240890 | 54.9 | 46.7 |
| 2-(4-carbamimidoylphenyl)benzothiophene-5-carboximidamide | 240891 | 40.3 | 99.4 |
| 2-(4-carbamimidoylphenyl)benzofuran-5-carboximidamide | 240893 | 47.4 | 86.4 |
| 2-(4-carbamimidoylphenyl)-3H-benzoimidazole-5-carboximidamide | 240894 | | 89.7 |
| 2-(4-carbamimidoylphenyl)indazole-5-carboximidamide | 240895 | 32.2 | 99.7 |
| 2-[4-(4-carbamimidoylphenoxy)phenyl]-1H-indole-6-carboximidamide | 240898 | | 98.1 |
| 2-[(E)-2-(5-carbamimidoylbenzofuran-2-yl)ethenyl]benzofuran-5-carboximidamide | 240899 | 47.4 | |
| 2-[(E)-2-(5-carbamimidoylbenzothiophen-2-yl)ethenyl]benzofuran-5-carboximidamide | 266472 | 67.5 | |
| 4-[3-(4-carbamimidoylphenyl)oxazol-5-yl]benzenecarboximidamide | 240900 | | 79.9 |
| 6-(4,5-dihydro-1H-imidazol-2-yl)-2-[4-(4,5-dihydro-1H-imidazol-2-yl)phenyl]-1H-indole | 278995 | | 99.3 |
| 2-[2-[4-(4,5-dihydro-1H-imidazol-2-yl)phenyl]benzofuran-5-yl]-4,5-dihydro-1H-imidazole | 278997 | 34.1 | |
| 2-[2-[(E)-2-[5-(4,5-dihydro-1H-imidazol-2-yl)benzofuran-2-yl]ethenyl]benzofuran-5-yl]-4,5-dihydro-1H-imidazole | 278999 | 55.6 | |
| 2-[(E)-2-(5-carbamimidoylbenzofuran-2-yl)ethenyl]-1H-indole-5-carboximidamide | 290107 | 33.6 | |
| 5-(4,5-dihydro-1H-imidazol-2-yl)-2-[(E)-2-[5-(4,5-dihydro-1H-imidazol-2-yl)benzofuran-2-yl]ethenyl]-1H-indole | 290108 | 45.0 | 45.1 |
| 5-(4,5-dihydro-1H-imidazol-2-yl)-N-[4-(4,5-dihydro-1H-imidazol-2-yl)phenyl]benzofuran-2-carboxamide | 290111 | 40.0 | |
| 2-[(E)-2-(5-carbamimidoylbenzofuran-2-yl)ethenyl]benzofuran-5-carboximidamide; methanesulfonic acid | 291103 | 39.6 | |
| 2-[(E)-2-(6-carbamimidoylbenzofuran-2-yl)ethenyl]benzofuran-6-carboximidamide | 294199 | 68.8 | 40.9 |
| 2-[(E)-2-(5-carbamimidoylbenzofuran-2-yl)ethenyl]benzofuran-6-carboximidamide | 294202 | 71.2 | |
| 6-(4,5-dihydro-1H-imidazol-2-yl)-N-[4-(4,5-dihydro-1H-imidazol-2-yl)phenyl]-1H-indole-2-carboxamide | 294206 | 61.53 | 86.0 |
| 6-(4,5-dihydro-1H-imidazol-2-yl)-N-[4-(4,5-dihydro-1H-imidazol-2-yl)phenyl]benzofuran-2-carboxamide | 294208 | 38.76 | |
| 3-amino-2-(4-carbamimidoylphenyl)-1H-indole-6-carboximidamide | 300509 | | 84.9 |
| 4-[5-(4-carbamimidoylphenyl)thiophen-2-yl]benzenecarboximidamide | 300510 | 59.7 | 89.9 |
| 2-[(1E,3E)-4-(5-carbamimidoylbenzofuran-2-yl)buta-1,3-dienyl]benzofuran-5-carboximidamide | 300511 | 49.2 | |
| N,N'-bis(3-dimethylaminopropyl)-3,9-dimethylquinolino[8,7-h]quinoline-1,7-diamine | 306365 | 99 | 99 |
| 2-[2-[4-(4,5-dihydro-1H-imidazol-2-yl)phenyl]benzothiophen-5-yl]-4,5-dihydro-1H-imidazole | 308569 | 35.3 | 95.8 |
| 2-[2-[(E)-2-[4-(4,5-dihydro-1H-imidazol-2-yl)phenyl]ethenyl]benzofuran-5-yl]-4,5-dihydro-1H-imidazole | 308570 | 30.7 | |
| 2-[2-[(1E,3E)-4-[5-(4,5-dihydro-1H-imidazol-2-yl)benzofuran-2-yl]buta-1,3-dienyl]benzofuran-5-yl]-4,5-dihydro-1H-imidazole | 308571 | 61.2 | |
| 2-[(1E,3E)-4-(4-carbamimidoylphenyl)buta-1,3-dienyl]benzofuran-5-carboximidamide | 308572 | 32.8 | |
| 2-[2-[(1E,3E)-4-[4-(4,5-dihydro-1H-imidazol-2-yl)phenyl]buta-1,3-dienyl]benzofuran-5-yl]-4,5-dihydro-1H-imidazole | 308573 | 54.2 | |
| 6-(4,5-dihydro-1H-imidazol-2-yl)-2-[6-(4,5-dihydro-1H-imidazol-2-yl)-1H-indol-2-yl]-1H-indole | 330688 | 51.3 | 84.9 |
| 2-(diaminomethylidene)indole-6-carboximidamide | 330689 | | 89.9 |
| 2-[[2-[4-[(E)-(diaminomethylidenehydrazinylidene)methyl]phenyl]benzothiophen-6-yl]methylideneamino]guanidine | 341909 | 57.5 | 95.8 |
| 6-(4,5-dihydro-1H-imidazol-2-yl)-3-[6-(4,5-dihydro-1H-imidazol-2-yl)-1H-indol-2-yl]-2-[4-(4,5-dihydro-1H-imidazol-2-yl)phenyl]-1H-indole | 341911 | 33.2 | |

TABLE 1-continued

| Compound | NSC Number* | EBOV % Inhibition (20 μM) | Monkey Pox % Inhibition (20 μM) |
|---|---|---|---|
| 6-(4,5-dihydro-1H-imidazol-2-yl)-3-[6-(4,5-dihydro-1H imidazol-2-yl)-1H-indol-2-yl]-2-[4-(4,5-dihydro-1H-imidazol-2-yl)phenyl]-1H-indole | 352341 | 41.2 | |
| 2-(2-(5-(amino(imino)methyl)-1-benzofuran-2-yl)vinyl)-1H-benzimidazole-5-carboximidamide | 369723 | 94.0 | |
| 2-[(Z)-2-(5-carbamimidoylbenzofuran-2-yl)ethenyl]benzofuran-5-carboximidamide | 607617 | 48.9 | |
| $N^6$-(2-((3-(diethylamino)propyl)amino)-6-methyl-4-pyrimidinyl)-2-methyl-4,6-quinolinediamine | 23767 | 74.1 | |
| 2,3-bis((2-hydroxyethyl)thio)naphthoquinone | 95397 | 75.3 | |
| N-(3-((4-chlorophenyl)thio)-1,4-dioxo-1,4-dihydro-2-naphthalenyl)acetamide | 128981 | 97.7 | |
| 5-Benzofurancarboximidamide, 2,2'-(1,2-ethenediyl)bis-, dihydrochloride | 240899 | 72.3 | |
| 5,11-dimethyl-6H-pyrido[4,3-b]carbazol-9-ol | 264136 | 63.1 | |
| 5-Benzofurancarboximidamide, 2,2'-(1,2-ethenediyl)bis-, dimethanesulfonate | 291103 | 69.6 | |
| 4-(6-(4,5-dihydro-1H-imidazol-2-yl)-1H-indol-2-yl)phenylamine | 369715 | 56.8 | |

*The structural formulas of these compounds are known in the art and may be obtained from various sources including the World Wide Web at dtp.nci.nih.gov/dtpstandard/ChemData/index.jsp, ncbi.nlm.nih.gov/entrez/query.fcgi?CMD=&DB=PubMed, and cactus.nci.nih.gov/cgi-bin/lookup/search and are herein incorporated by reference.

After repeated dose response experiments, the three most potent compounds were identified as NSC 369723, NSC 294202, and NSC 128981. Vero-E6 cells were plated on 96 well plates at ($5 \times 10^4$ cells/well) in 100 μl cEMEM medium (EMEM (Invitrogen) with NEAA 41500-083 supplemented with 10% FBS (SH30071.03, HyClone) and 0.5% penicillin (P7794, Sigma Aldrich) and 0.5% streptomycin (S9137, Sigma Aldrich). Cells were cultured for 3 days at 37° C. in a humidified incubator (5% $CO_2$). Dilutions of the compounds were made at concentrations indicated on the X-axis of FIG. 5 in cEMEM medium under aseptic conditions. Media were removed from the wells of the 96 well plates and replaced by 100 μl of media containing the compounds at various concentrations including a control containing no compound. Each compound concentration was repeated in three wells (triplicate). The cells were then incubated again in the incubator at 37° C. for an additional 18 to 24 hours. After adding 50 μl of GFP-EBOV ($10^6$ infectious virus particles per ml) to each well, the cells were incubated at 37° C. (5% $CO_2$) for 40 to 48 hours. Then the media was aspirated and the assay plates with the cells were submerged in 4% formaldehyde in PBS buffer in plastic bags (one assay plate per bag) to inactivate the virus. The bags were sealed and incubated at room temperature for three days. Then, the formaldehyde solution was removed from the assay plates and replaced with 100 μl of PBS/well. The assay plates were then subjected to high throughput screening to measure the percent of the infected cells in each well. Specifically, the cells were imaged with a 10× objective lens on a Discovery-1 (Molecular Devices Corporation, Downingtown, Pa.) high content imager. The Discovery-1 was programmed to sequentially acquire images first with a DAPI filter set then with a GFP filter set for each of 9 image fields per well on a 96-well culture plate. Analysis was performed on MetaXpress software by modifying a "live dead" analysis module to count the total number of cells (based on the number of cell nuclei) and the number of infected cells (based on the number of nuclei associated with cytoplasmic GFP fluorescence). These numbers were used to calculate percent infection.

The average percent infected in each well was calculated from 9 individual spots read in each well. The percent infected data from the drug-treated wells were then normalized to the control by setting the percent infected cells in control wells (average of three wells) as 100 and calculating the efficiency of infection in drug-treated wells as percent of control infection according to the following equation:

$$\% \text{ of control infection} = \left( \frac{\% \text{ infected in experimental well}}{\text{mean \% infected in control wells}} \right) \times 100$$

Figure 2:
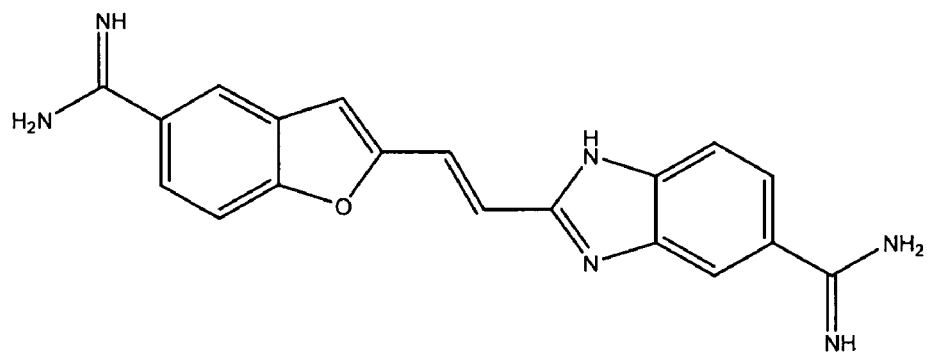
FIG. 2 shows the structural formulas for NSC 369723, NSC 294202, and NSC 128981.
Figure 2:
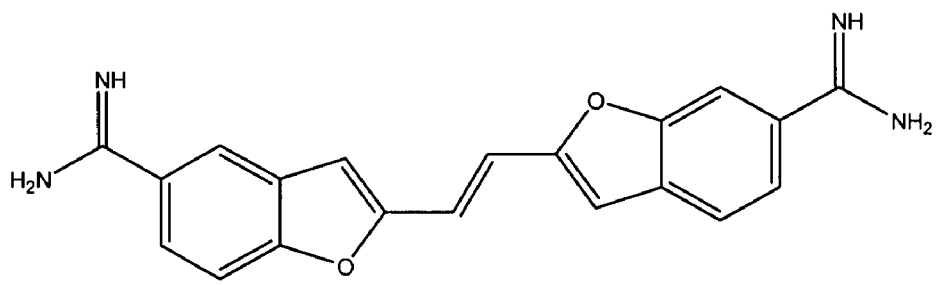
Figure 2:
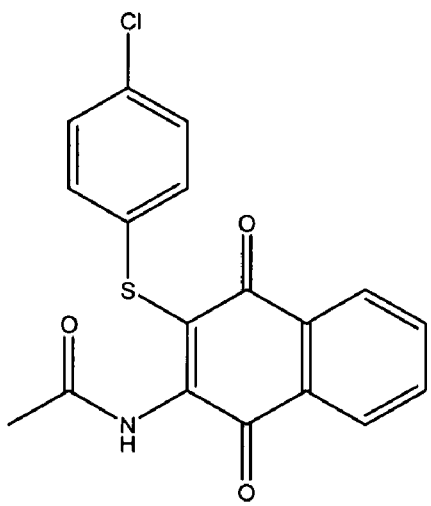

The data were then graphed by plotting % of control infection on Y-axis against drug concentration on the X-axis. $IC_{50}$ was read from the graphs. The $IC_{50}$ concentrations were found to be about 4 μM for NSC 369723, about 6 μM for NSC 294202, and about 15 μM for NSC 128981. The structural formulas for NSC 369723, NSC 294202, and NSC 128981 are shown in FIG. 2.

Because of the similarity of their structural formulas, and the lower $IC_{50}$, NSC 369723 and NSC 294202 were selected for in vivo experiments to determine their ability to protect mice from lethal infection with mouse-adapted Ebola Zaire virus. In these experiments, groups of 10 C57BL/6 mice each were treated with 10 mg/kg of NSC 369723 or NSC 294202 at 1 hour before and 48 hours and 96 hours after challenge with 1000 pfu of the mouse-adapted Ebola Zaire virus. The control group received 10% DMSO in PBS. Injections and challenge were performed intraperitoneally.

Figure 3:
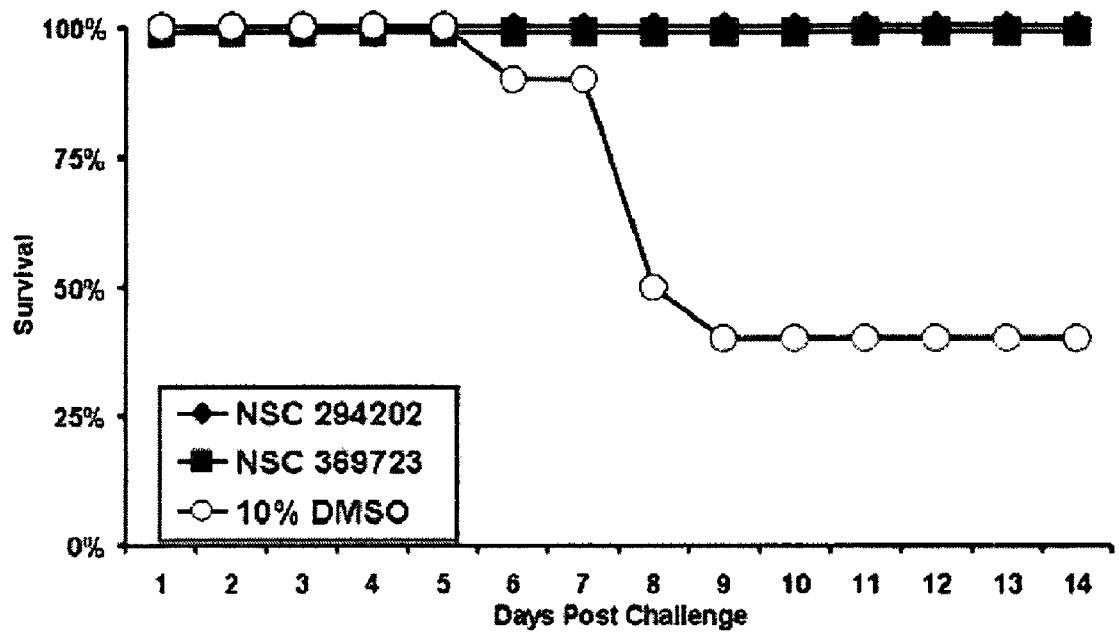
FIG. 3 shows that mice treated with either NSC 369723 or NSC 294202 were completely protected from lethal challenge, whereas the control mice showed only 40% survival.
Figure 4A:
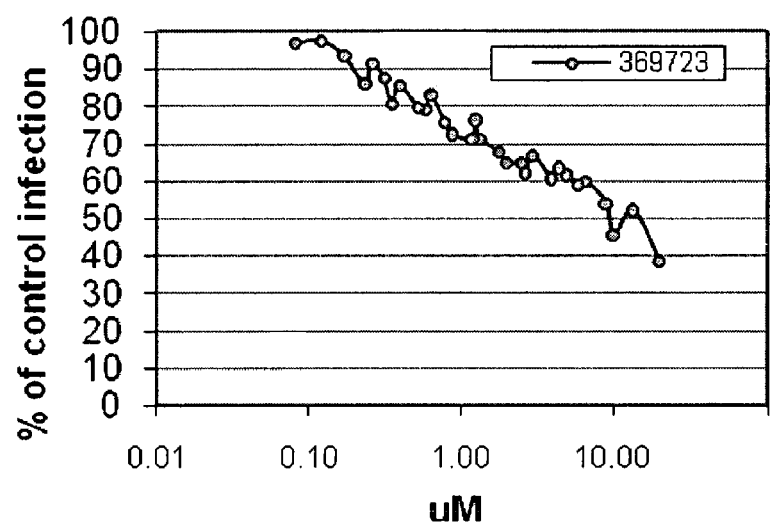
FIG. 4A shows that NSC 369723 exhibits dose dependent antiviral activity toward EBOV-GFP. Data are summary of about 3 to about 20 individual experiments.
Figure 4B:
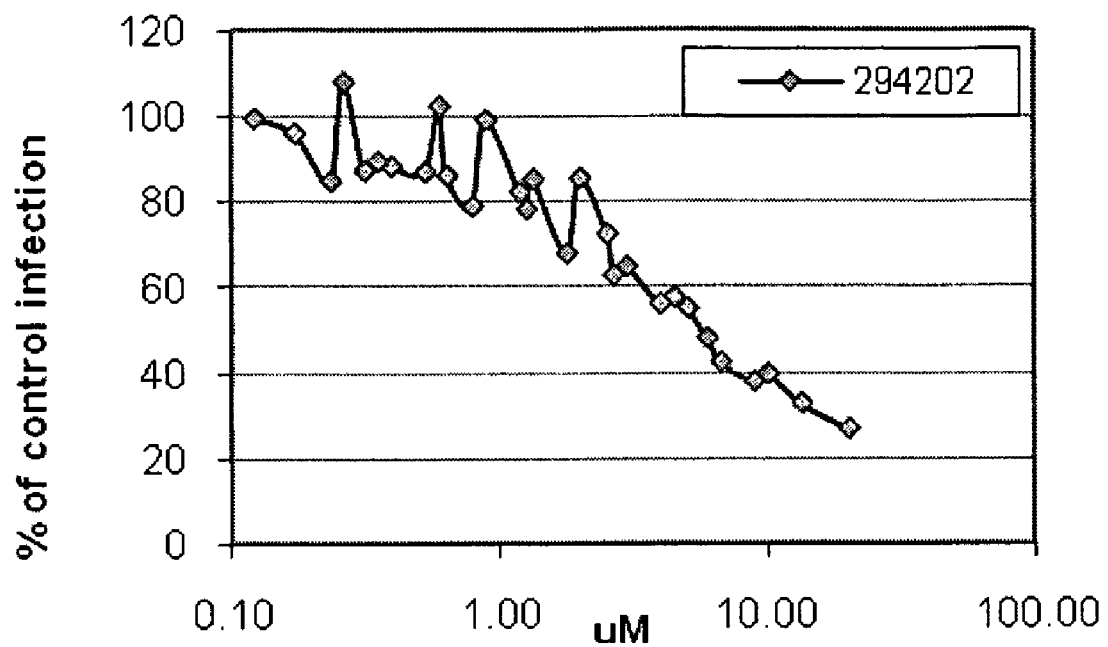
FIG. 4B shows that NSC 294202 exhibits dose dependent antiviral activity toward EBOV-GFP. Data are summary of about 3 to about 20 individual experiments.
Figure 4C:
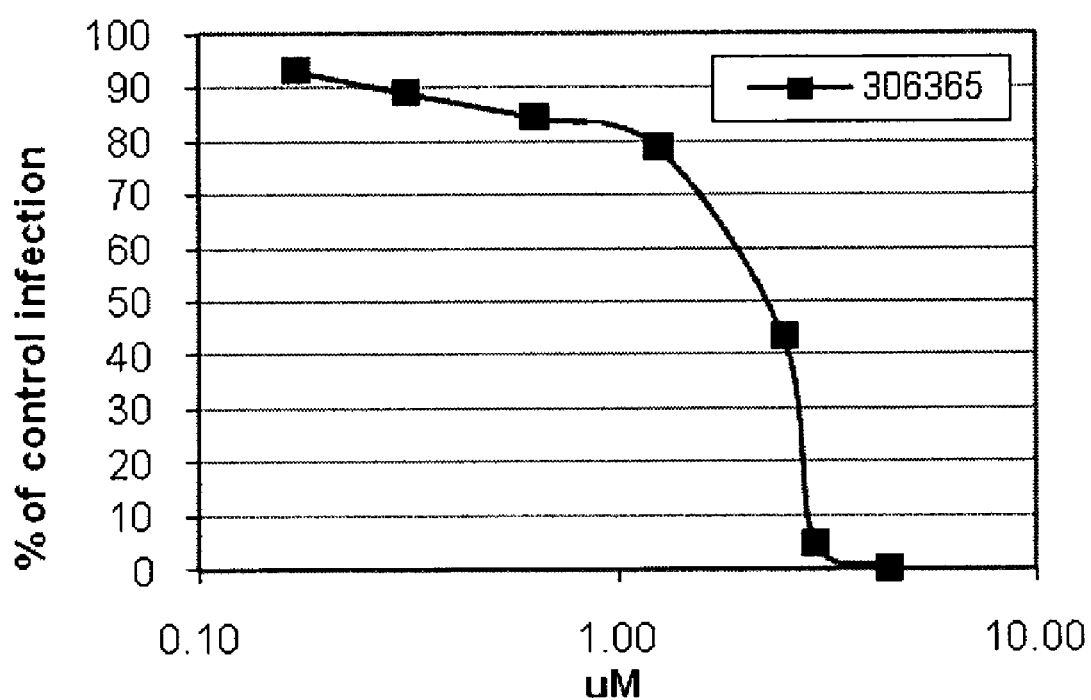
FIG. 4C shows that NSC 306365 exhibits dose dependent antiviral activity toward EBOV-GFP. Data are summary of about 3 to about 20 individual experiments.
Figure 4D:
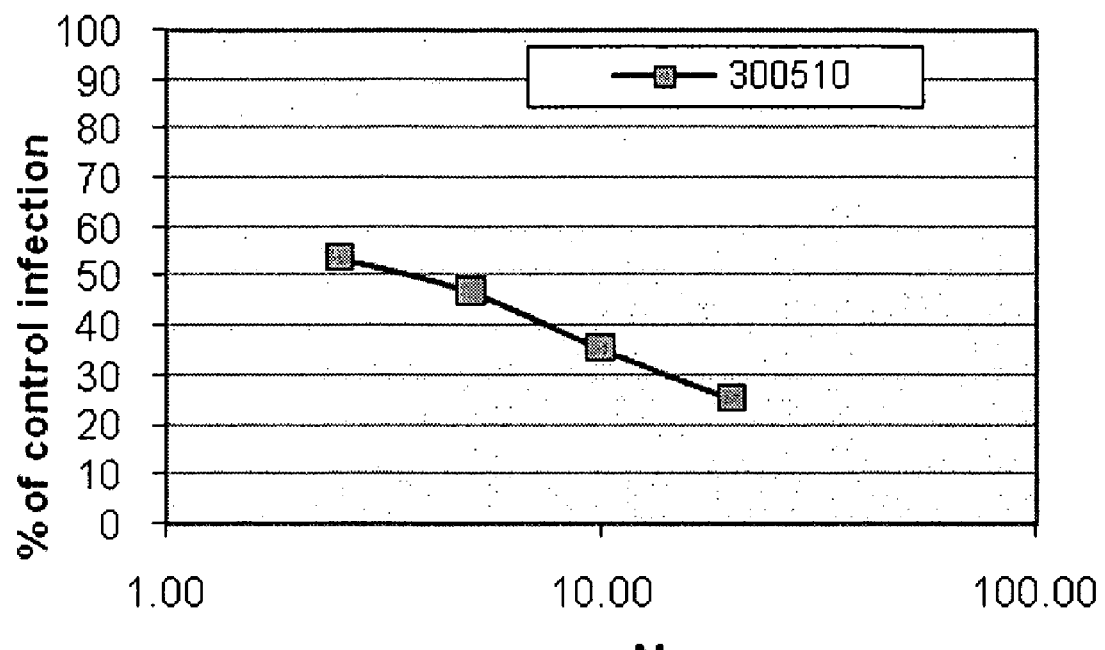
FIG. 4D shows that NSC 300510 exhibits dose dependent antiviral activity toward EBOV-GFP. Data are summary of about 3 to about 20 individual experiments.
Figure 4E:
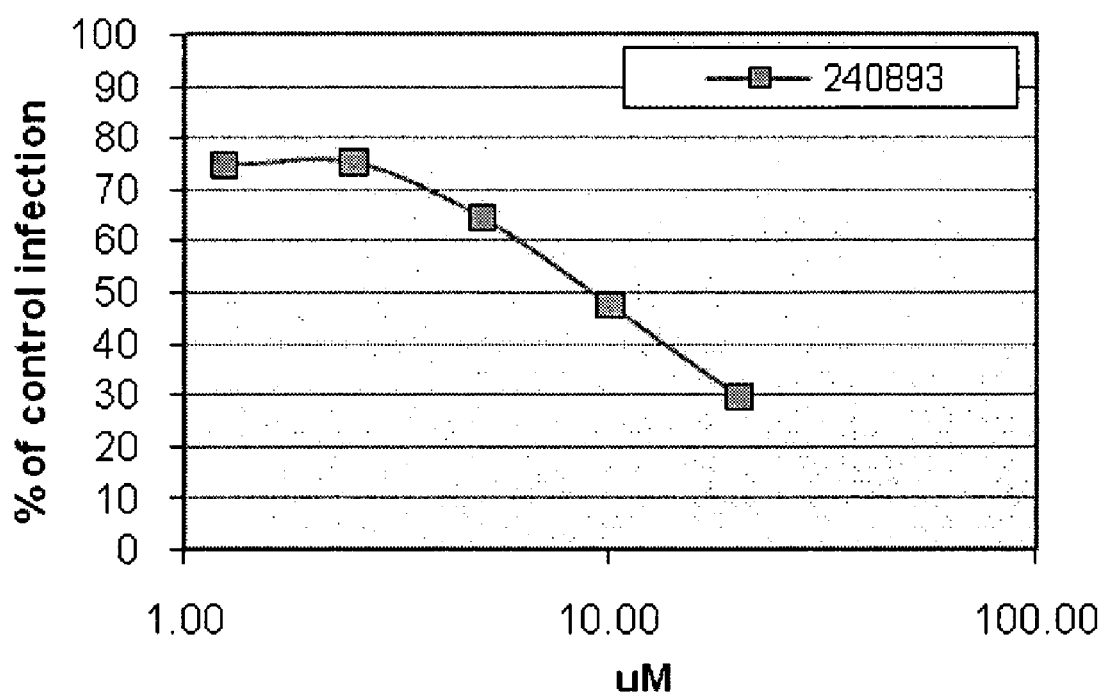
FIG. 4E shows that NSC 240893 exhibits dose dependent antiviral activity toward EBOV-GFP. Data are summary of about 3 to about 20 individual experiments.
Figure 4F:
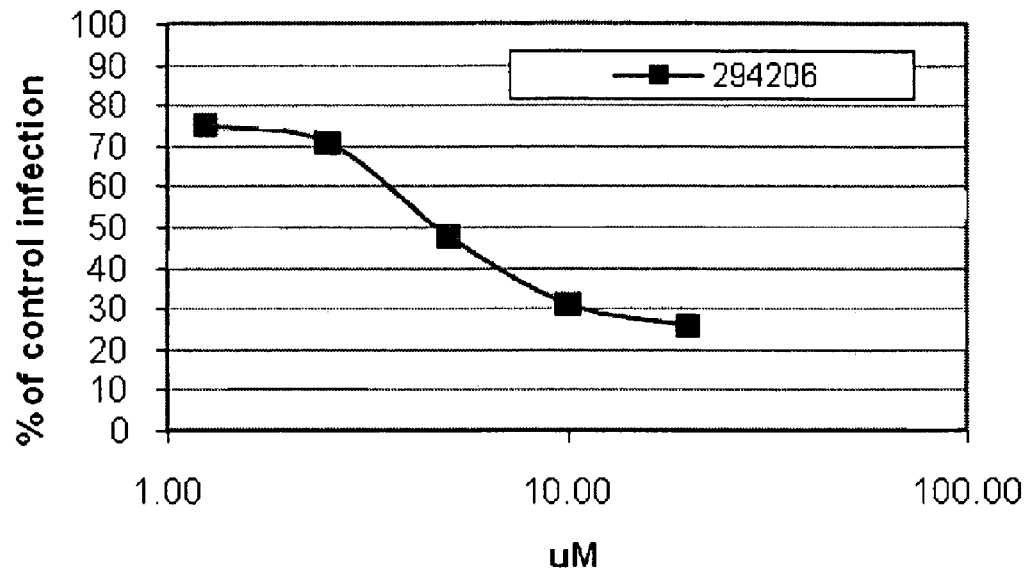
FIG. 4F shows that NSC 294206 exhibits dose dependent antiviral activity toward EBOV-GFP. Data are summary of about 3 to about 20 individual experiments.

As shown in FIG. 3, C57BL/6 mice treated with either compound were completely protected from lethal challenge, whereas the control mice showed only 40% survival. In addition, no sign of infection was observed in any of the treated mice. In contrast, however, all the control mice exhibited symptoms of infection. Thus, NSC 369723 and NSC 294202, as well as the other compounds set forth in Table 1, may be used to prevent, treat, or inhibit infection by EBOV in a subject.

Therefore, the compounds of the present invention have a structural formula selected from the group consisting of:

Structural Formula 1

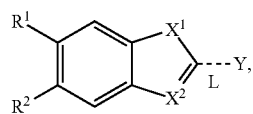

Structural Formula 2

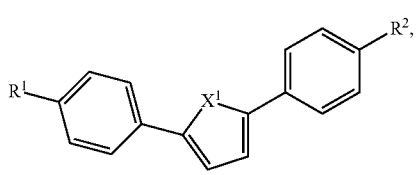

Structural Formula 3

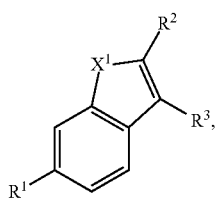

Structural Formula 4

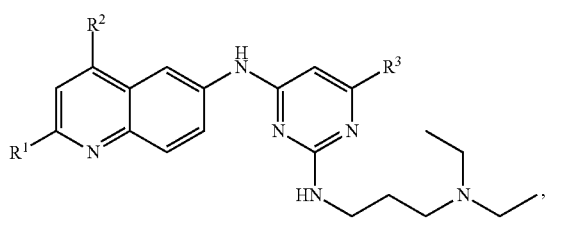

Structural Formula 5

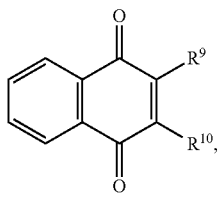

Structural Formula 6

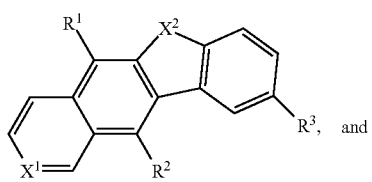, and

Structural Formula 7

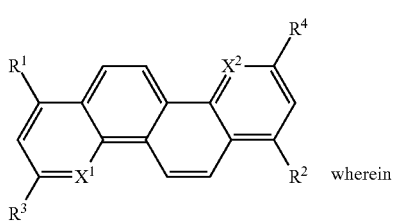

wherein

Y is 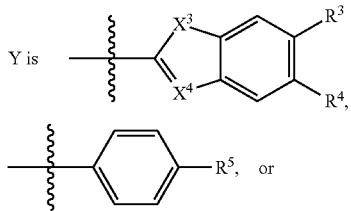

-continued

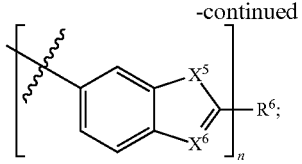

n is 1 or 2;

$X^1$, $X^2$, $X^3$, $X^4$, $X^5$ and $X^6$ are each independently C, N, S, O, $SO_2$, $CR^7$ or $NR^8$;

L is a linker which may be a direct bond or

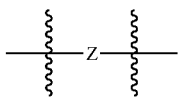

where Z is an optionally substituted alkyl, alkenyl, dialkenyl, trialkenyl, aryl, amide;

$R^1$, $R^2$, $R^3$, $R^4$, $R^5$, $R^6$ and $R^7$ are each independently hydrogen, amino, amine (e.g. nitrogen) with stabilized carbocations, carboxyl, optionally substituted alkyl, alkenyl, alkynyl, cycloalkyl, heterocycloalkyl, aryl, heteroaryl, alkoxy, aryoxy, cycloalkoxy, heteroaryloxy, alkoxycarbonyl, alkylamino, carbamoyl, alkylaminocarbonyl, alkylsulfhydryl, alkylhydroxymate, or an amide possessing alkyl substituent(s);

$R^8$ is hydrogen, OH, a halogen, or an optionally substituted alkyl; and $R^9$ and $R^{10}$ are each independently optionally substituted mercapto alkyl, alkenyl, alkynyl, cycloalkyl, heterocycloalkyl, aryl, heteroaryl, alkoxy, aryoxy, cycloalkoxy, heteroaryloxy, alkoxycarbonyl, alkylamino, carbamoyl, alkylaminocarbonyl, alkylsulfhydryl, or alkylhydroxymate.

In some embodiments, at least one of $X^1$ or $X^2$ is N, S, O, $SO_2$, or $NR^8$.

In some embodiments, $R^1$ is hydrogen, amidine, 2-imidazoline, amino, guanidine, methyl, aminomethyl-hydroxamine, or methylamine-guanidine.

In some embodiments, $R^2$ is hydrogen, amidine, 2-imidazoline, amino, guanidine, methyl, aminomethyl-hydroxamine, or methylamine-guanidine.

In some embodiments, $R^3$ is hydrogen, amidine, 2-imidazoline, amino, guanidine, methyl, aminomethyl-hydroxamine, or methylamine-guanidine.

In some embodiments, $R^4$ is hydrogen, amidine, 2-imidazoline, amino, guanidine, methyl, aminomethyl-hydroxamine, or methylamine-guanidine.

In some embodiments, $R^5$ is hydrogen, amidine, 2-imidazoline, amino, guanidine, methyl, aminomethyl-hydroxamine, methylamine-guanidine, 4-oxy-benzamidine, 1H-indole-6-caboxamidine, or 1H-indole-5-carboxamidine.

In some embodiments, $R^6$ is hydrogen, amidine, benzamidine, benzimidazoline, imidazoline, guanidine, imidazole, oxazole, benzofuran-2-yl-imidazoline, benzofuran-2-yl-amidine, benzofuran-2-yl-guanidine, benzothiophene-2-yl-imidazoline, benzothiophene-2-yl-amidine, benzene-2-yl-amidine, benzofuran-2-yl-imidazole, or benzofuran-2-yl-oxazole.

In some embodiments, $X^1$ is N, NH, S, O, $SO_2$, CH, C—$CH_3$, C-phenyl, N-ethanol, N-chloroethyl, C-amino, C-(2-indole-6-imidazoline), C-(2-indole-6-amidine), C-(2-indole-5-imidazoline), or C-(2-indole-5-amidine).

In some embodiments, $X^2$ is N, NH, S, O, $SO_2$, CH, C—$CH_3$, C-phenyl, N-ethanol, N-chloroethyl, C-amino, C-(2-indole-6-imidazoline), C-(2-indole-6-amidine), C-(2-indole-5-imidazoline), or C-(2-indole-5-amidine).

In some embodiments, $X^3$ is N, NH, S, O, $SO_2$, or CH.
In some embodiments, $X^4$ is N, NH, S, O, $SO_2$, or CH.
In some embodiments, $X^5$ is N, NH, S, O, $SO_2$, or CH.
In some embodiments, $X^6$ is N, NH, S, O, $SO_2$, or CH.
In some embodiments, at least one of $R^1, R^2, R^3, R^4, R^5, R^6$ or $R^7$ is —H, —$CH_3$,

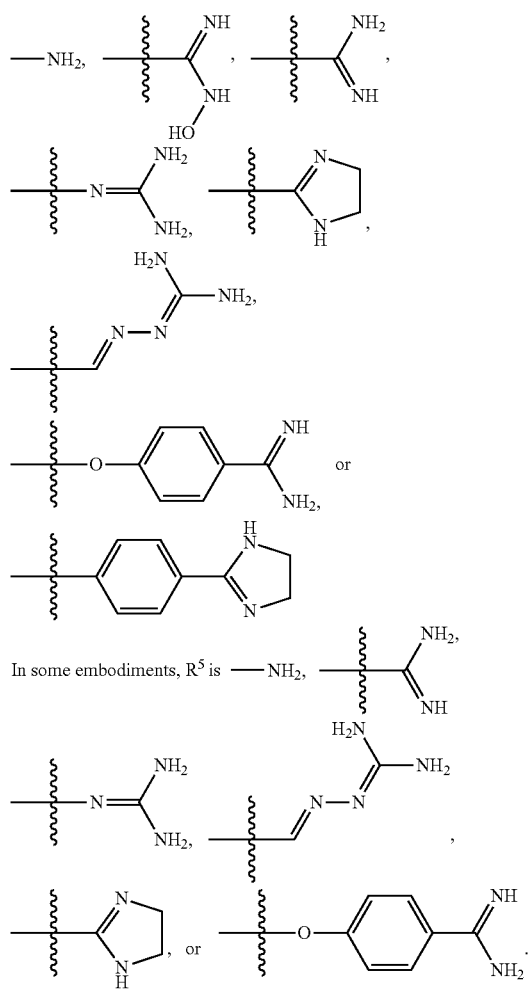

In some embodiments, $R^5$ is —$NH_2$,
In some embodiments, $R^6$ is

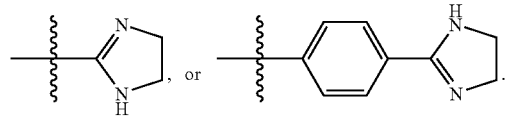

In some embodiments, $R^7$ is —H, —$CH_3$, —$NH_2$,

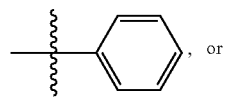, or

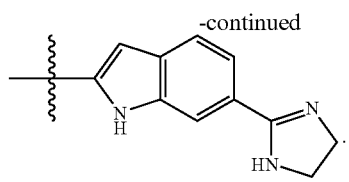

In some embodiments, $R^8$ is —H, —$(CH_2)_2OH$, or —$(CH_2)_2Cl$.

In some embodiments, L is a direct bond,

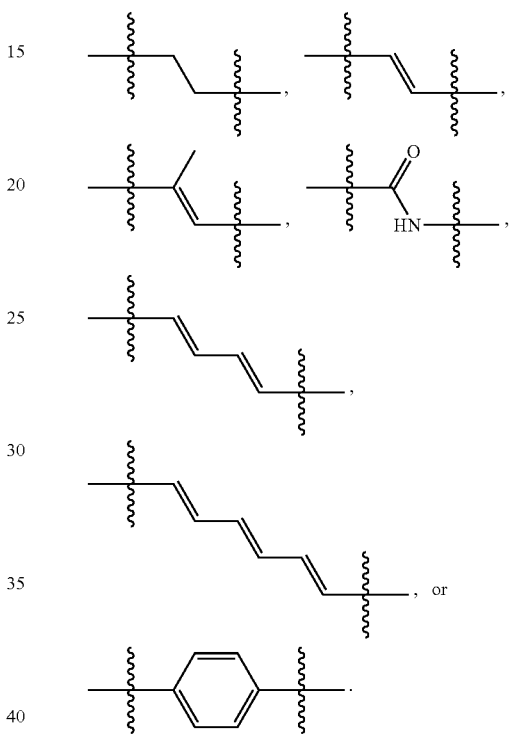

In some embodiments, compounds of the present invention have the following structural formulae:

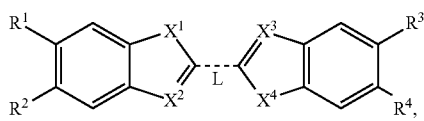

(i)

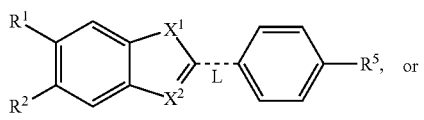

(ii)

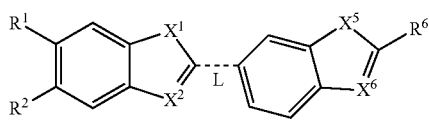

(iii)

wherein
n is 1 or 2;
$X^1, X^2, X^3, X^4, X^5$ and $X^6$ are each independently N, S, O, $SO_2$, $CR^7$ or $NR^8$ and at least one of $X^1$ or $X^2$ is N, S, O, $SO_2$, or $NR^8$;

L is a linker which may be a direct bond or

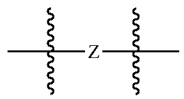

where Z is an optionally substituted alkyl, alkenyl, dialkenyl, trialkenyl, or aryl, or C(O)NH; and $R^1$, $R^2$, $R^3$, $R^4$, $R^5$, $R^6$ and $R^7$ are each independently hydrogen, amino, amine (e.g. nitrogen) with stabilized carbocations, carboxyl, optionally substituted alkyl, alkenyl, alkynyl, cycloalkyl, heterocycloalkyl, aryl, heteroaryl, alkoxy, aryoxy, cycloalkoxy, heteroaryloxy, alkoxycarbonyl, alkylamino, carbamoyl, alkylaminocarbonyl, alkylsulfhydryl, alkylhydroxymate, or an amide possessing alkyl substituent(s); and $R^8$ is hydrogen, OH, a halogen, or an optionally substituted alkyl.

In some embodiments, compounds of the present invention have the following structural formulae:

Structural Formula A

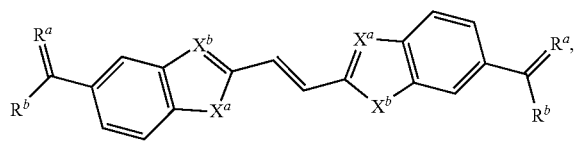

Structural Formula B

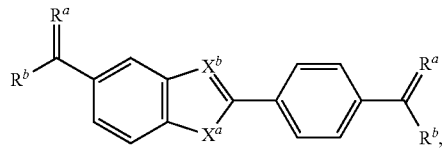

Structural Formula C

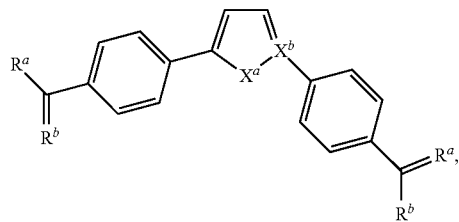

Structural Formula D

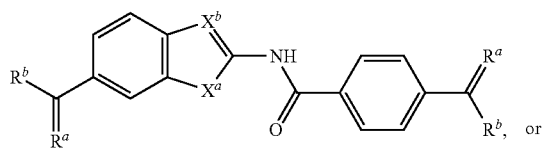

Structural Formula E

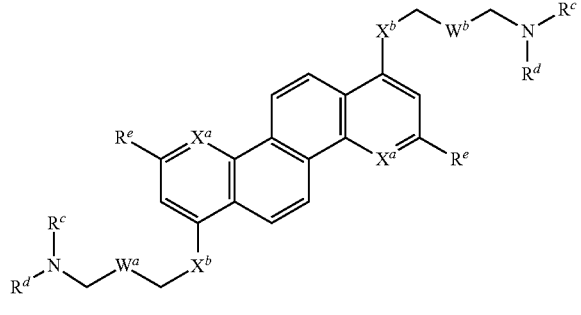

wherein $X^a$ and $X^b$ are each independently C, N, NH, S, O, or CH;

$W^a$ and $W^b$ are each independently alkyl, alkenyl, alkynyl, cycloalkyl, heterocycloalkyl, or aryl;

$R^a$ and $R^b$ are each independently N, NH, O, OH, an oxime, an alkyloxime, an alkyl or a fused ring system such that $R^a$—$CH_2$—$CH_2$—$R^b$ form an imidazole ring; and $R^c$ and $R^d$ are each independently alkyl, alkenyl, alkynyl, cycloalkyl, heterocycloalkyl, aryl, heteroaryl, alkoxy, aryoxy, cycloalkoxy, heteroaryloxy, alkoxycarbonyl, alkylamino, carbamoyl, alkylaminocarbonyl, alkylsulfhydryl, or part of fused ring systems such that $R^c$ and $R^d$ form a cycloalkyl or heterocycloalkyl ring.

Compounds and compositions of the present invention also include those provided in U.S. Publication Nos. 20070112048 and 20070112049, which are herein incorporated by reference.

In accordance with a convention used in the art,

is used in structural formulas herein to depict the bond that is the point of attachment of the moiety or substituent to the core or backbone structure. It is noted that in the structural formulas of the present invention, the bond orders of the specified rings may vary when the various heteroatoms introduce specific requirements to satisfy aromaticity, prevent antiaromaticity, and stabilize tautomeric forms due to localization. Thus, the appropriate bond orders of the ring structures in the structural formulas of the present invention are contemplated herein.

Where chiral carbons are included in chemical structures, unless a particular orientation is depicted, both stereoisomeric forms are intended to be encompassed.

A "halo" or "halogen" means fluorine, bromine, chlorine, and iodine.

An "alkyl" is intended to mean a straight or branched chain monovalent radical of saturated and/or unsaturated carbon atoms and hydrogen atoms, such as methyl (Me), ethyl (Et), propyl (Pr), isopropyl (i-Pr), butyl (n-Bu), isobutyl (i-Bu), t-butyl (t-Bu), (sec-Bu), and the like, which may be unsubstituted (i.e., contain only carbon and hydrogen) or substituted by one or more suitable substituents as defined below. A "lower alkyl group" is intended to mean an alkyl group having from 1 to 8 carbon atoms in its chain.

A "haloalkyl" refers to an alkyl that is substituted with one or more same or different halo atoms, e.g., —$CH_2Cl$, —$CF_3$, —$CH_2CF_3$, —$CH_2CCl_3$, and the like.

An "alkenyl" means straight and branched hydrocarbon radicals having from 2 to 8 carbon atoms and at least one double bond such as ethenyl, 3-buten-1-yl, 2-ethenylbutyl, 3-hexen-1-yl, and the like. The term "alkenyl" includes, cycloalkenyl, and heteroalkenyl in which 1 to 3 heteroatoms selected from O, S, N or substituted nitrogen may replace carbon atoms.

An "alkynyl" means straight and branched hydrocarbon radicals having from 2 to 8 carbon atoms and at least one triple bond and includes, but is not limited to, ethynyl, 3-butyn-1-yl, propynyl, 2-butyn-1-yl, 3-pentyn-1-yl, and the like.

A "cycloalkyl" is intended to mean a non-aromatic monovalent monocyclic or polycyclic radical having from 3 to 14 carbon atoms, each of which may be saturated or unsaturated, and may be unsubstituted or substituted by one or more suitable substituents as defined herein, and to which may be fused one or more aryl groups, heteroaryl groups, cycloalkyl groups, or heterocycloalkyl groups which themselves may be unsubstituted or substituted by one or more substituents. Examples of cycloalkyl groups include cyclopropyl, cycloheptyl, cyclooctyl, cyclodecyl, cyclobutyl, adamantyl, norpinanyl, decalinyl, norbornyl, cyclohexyl, and cyclopentyl.

A "heterocycloalkyl" is intended to mean a non-aromatic monovalent monocyclic or polycyclic radical having 1-5 heteroatoms selected from nitrogen, oxygen, and sulfur, and may be unsubstituted or substituted by one or more suitable substituents as defined herein, and to which may be fused one or more aryl groups, heteroaryl groups, cycloalkyl groups, or heterocycloalkyl groups which themselves may be unsubstituted or substituted by one or more substituents. Examples of heterocycloalkyl groups include oxiranyl, pyrrolidinyl, piperidyl, tetrahydropyran, and morpholinyl.

An "aryl" (Ar) is intended to mean an aromatic monovalent monocyclic or polycyclic radical comprising generally between 5 and 18 carbon ring members, which may be unsubstituted or substituted by one or more suitable substituents as defined herein, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Examples include phenyl, biphenyl, 1,2,3,4-tetrahydronaphthyl, naphthyl, anthryl, and phenanthryl.

A "heteroaryl" is intended to mean an aromatic monovalent monocyclic or polycyclic radical comprising generally between 4 and 18 ring members, including 1-5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Examples include thienyl, furanyl, thiazolyl, triazolyl, imidazolyl, isoxazolyl, oxadiazolyl, tetrazolyl, pyridyl, pyrrolyl, thiadiazolyl, oxadiazolyl, oxathiadiazolyl, thiatriazolyl, pyrimidinyl, isoquinolinyl, quinolinyl, napthyridinyl, phthalimidyl, benzimidazolyl, and benzoxazolyl.

A "hydroxy" is intended to mean the radical —OH.

An "alkoxy" is intended to mean the radical —OR, where R is an alkyl group. Exemplary alkoxy groups include methoxy, ethoxy, propoxy, and the like.

A "hydroxyalkyl" means an alkyl that is substituted with one, two, or three hydroxy groups, e.g. hydroxymethyl, 1 or 2-hydroxyethyl, 1,2-, 1,3-, or 2,3-dihydroxypropyl, and the like.

A "haloalkoxy" refers to an —O-(haloalkyl) group. Examples include trifluoromethoxy, tribromomethoxy, and the like.

A "cycloalkoxy" is intended to mean the radical —OR, where R is acycloalkyl or heterocycloalkyl group.

An "aryloxy" is intended to mean the radical —OR, where R is an aryl or heteroaryl group. Examples include phenoxy, pyridinyloxy, furanyloxy, thienyloxy, pyrimidinyloxy, pyrazinyloxy, and the like.

An "acyl" is intended to mean a —C(O)—R radical, where R is an alkyl or aryl, bonded through a carbonyl group. Acyl groups include acetyl, benzoyl, and the like.

An "aralkyl" means an alkyl that is substituted with an aryl group. Examples include —CH$_2$-phenyl, —(CH$_2$)$_2$-phenyl, —(CH$_2$)$_3$-phenyl, —CH$_3$CH(CH$_3$)CH$_2$-phenyl, and the like.

A "heteroaralkyl" group means an alkyl that is substituted with a heteroaryl group. Examples include —CH$_2$-pyridinyl, —(CH$_2$)$_2$-pyrimidinyl, —(CH$_2$)$_3$-imidazolyl, and the like.

A "carboxy" is intended to mean the radical —C(O)OH.

An "alkoxycarbonyl" is intended to mean the radical —C(O)OR, where R is an alkyl group. Examples include methoxycarbonyl, ethoxycarbonyl, and the like.

An "amino" is intended to mean the radical —NH$_2$.

An "amine with stabilized carbocations" are comprised of two or more NH$_2$ groups that contribute lone pairs to configure a highly stabilized carbocation. Examples include amidines and guanidines.

An "alkylamino" is intended to mean the radical —NHR, where R is an alkyl group or the radical —NR$^a$R$^b$, where R$^a$ and R$^b$ are each independently an alkyl group. Examples of alkylamino groups include methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino, N-n-hexyl-N-methylamino and the like.

An "alkylsulfhydryl" is intended to mean R—SH, where R is an alkyl group. Examples include methylsulfhydryl, ethylsulfhydryl, n-propylsulfhydryl, iso-propylsulfhydryl, n-butylsulfhydryl, iso-butylsulfhydryl, secondary-butylsulfhydryl, tertiary-butylsulfhydryl. Preferable alkylsulfhydryl groups are methylsulfhydryl, ethylsulfhydryl, n-propylsulfhydryl, n-butylsulfhydryl, and the like.

An "alkylhydroxymate" is intended to mean the radical R—C(O)NH—OH, where R is an alkyl group. Examples include methylhydroxymate, ethylhydroxymate, n-propylhydroxymate, iso-propylhydroxymate, n-butylhydroxymate, iso-butylhydroxymate, secondary-butylhydroxymate, tertiary-butylhydroxymate. Preferable alkylhydroxymate groups are methylhydroxymate, ethylhydroxymate, n-propylhydroxymate, n-butylhydroxymate, and the like. A "carbamoyl" is intended to mean the radical —C(O)NH$_2$.

An "alkylaminocarbonyl" is intended to mean the radical —C(O)NHR, where R is an alkyl group or the radical —C(O)NR$^a$R$^b$, where R$^a$ and R$^b$ are each independently an alkyl group. Examples include methylaminocarbonyl, ethylaminocarbonyl, dimethylaminocarbonyl, methylethylaminocarbonyl, and the like.

A "mercapto" is intended to mean the radical —SH.

An "alkylthio" is intended to mean the radical —SR, where R is an alkyl or cycloalkyl group. Examples of alkylthio groups include methylthio, ethylthio, n-propylthio, isopropylthio, tert-butylthio, n-pentylthio, n-hexylthio, cyclopropylthio, cyclobutylthio, cyclopentylthio, cyclohexylthio, and the like.

An "arylthio" is intended to mean the radical —SR, where R is an aryl or heteroaryl group. Examples include phenylthio, pyridinylthio, furanylthio, thienylthio, pyrimidinylthio, and the like.

A "thioacyl" is intended to mean a —C(S)—R radical, where R is an alkyl or aryl, bonded through a thiol group.

An "alkylsulfonyl" is intended to mean the radical —SO$_2$R, where R is an alkyl group. Examples include methylsulfonyl, ethylsulfonyl, n-propylsulfonyl, iso-propylsulfonyl, n-butylsulfonyl, iso-butylsulfonyl, secondary-butylsulfonyl, tertiary-butylsulfonyl. Preferable alkylsulfonyl groups are methylsulfonyl, ethylsulfonyl, n-propylsulfonyl, n-butylsulfonyl, and the like.

A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A "protecting group" is intended to refer to groups that protect one or more inherent functional group from premature reaction. Suitable protecting groups may be routinely selected by those skilled in the art in light of the functionality and particular chemistry used to construct the compound. Examples of suitable protecting groups are described, for example, in Greene and Wuts, Protective Groups in Organic Synthesis, 3$^{rd}$ edition, John Wiley and Sons, New York, N.Y. (1999).

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxyl groups, carboxyl groups, amino groups, alkylamino groups, dialkylamino groups, carbamoyl groups, arylthio groups, heteroarylthio groups, and the like.

In general, the various moieties or functional groups for variables in the formulae may be "optionally substituted" by one or more suitable "substituents". The term "substituent" or "suitable substituent" is intended to mean any suitable substituent that may be recognized or selected, such as through routine testing, by those skilled in the art. Illustrative examples of useful substituents are those found in the exemplary compounds that follow, as well as a halogen; $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl, aryl; aryl-lower alkyl; CO$_2$CH$_3$; CONH$_2$; OCH$_2$CONH$_2$; NH$_2$; SO$_2$NH$_2$; OCHF$_2$; CF$_3$; OCF$_3$; and the like. Such moieties may also be optionally substituted by a fused-ring structure or bridge, for example OCH$_2$—O. All of these substituents may optionally be further substituted with a substituent selected from groups such as hydroxyl groups, halogens, oxo groups, alkyl groups, acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

It is understood that while a compound of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Some of the compounds of the present invention may exist as single stereoisomers (i.e., essentially free of other stereoisomers), racemates, or mixtures of enantiomers, diastereomers, or both when they contain one or more stereogenic centers as designated by R or S according to the Cahn-Ingold-Prelog rules whether the absolute or relative configuration is known. All such single stereoisomers, racemates and mixtures thereof are intended to be within the scope of the present invention.

Some of the compounds in the present invention may exist as geometric isomers as the result of containing a stereogenic double bond. In such cases, they may exist either as pure or mixtures of cis or trans geometric isomers or (E) and (Z) designated forms according to the Cahn-Ingold-Prelog rules and include compounds that adopt a double bond configuration as a result of electronic delocalization.

As generally understood by those skilled in the art, an optically pure compound having one or more chiral centers (i.e., one asymmetric atom producing unique tetrahedral configuration) is one that consists essentially of one of the two possible enantiomers (i.e., is enantiomerically pure), and an optically pure compound having more than one chiral center is one that is both diastereomerically pure and enantiomerically pure. If the compounds of the present invention are made synthetically, they may be used in a form that is at least 90% optically pure, that is, a form that comprises at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

Additionally, the structural formulas herein are intended to cover, where applicable, solvated as well as unsolvated forms of the compounds. A "solvate" is intended to mean a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone. Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulas include compounds having the indicated structure, including the hydrated as well as the non-hydrated forms.

As indicated above, the compounds of the invention also include active tautomeric and stereoisomeric forms of the compounds of the present invention, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

Additionally, the compounds of the invention include pharmaceutically acceptable salts, multimeric forms, prodrugs, active metabolites, precursors and salts of such metabolites of the compounds of the present invention.

The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

The term "multimer" refers to multivalent or multimeric forms of active forms of the compounds of the invention. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to binding site interactions. Provision of such multivalent forms of active binding compounds with optimal spacing between the binding site moieties may enhance binding site interactions. See e.g. Lee et al., (1984) *Biochem.* 23:4255, which is herein incorporated by reference. The artisan may control the multivalency and spacing by selection of a suitable carrier moiety or linker units. Useful moieties include molecular supports comprising a multiplicity of functional groups that can be reacted with functional groups associated with the active compounds of the invention. A variety of carrier moieties may be used to build highly active multimers, including proteins such as BSA (bovine serum albumin), peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound, or a compound that is biologically active with respect to the intended pharmacodynamic effect. "A pharmaceutically active metabolite" is intended to mean a pharmacologically active product produced through metabolism in the body of a specified compound or salt thereof. Prodrugs and active metabolites of a compound may be identified using routine techniques known in the art. See, e.g., Bertolini, G. et al., (1997) J. Med. Chem. 40:2011-2016; Shan, D. et al., *J. Pharm. Sci.*, 86(7):765-767; Bagshawe K., (1995) Drug Dev. Res. 34:220-230; Bodor, N., (1984) Advances in Drug Res. 13:224-331; Bundgaard, H., *Design of Prodrugs* (Elsevier Press, 1985); and Larsen, I. K., *Design and Application of Prodrugs*, Drug Design and Development (Krogsgaard-Larsen et al., eds., Harwood Academic Publishers, 1991), which are herein incorporated by reference.

If the compound of the present invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the present invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from basic amino acids, such as lysine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of compounds that are solids, it is understood by those skilled in the art that the compound of the present invention and salts may exist in different crystal or polymorphic forms, all of which are intended to be within the scope of the present invention and specified structural formulas.

The compounds of the present invention are useful as antiviral compounds. A compound of the present invention may be used to prevent, inhibit, or reduce the viral activity of a virus or treat an infection by at least one virus, such as one belonging to double-stranded DNA viruses (e.g. Adenoviruses, Herpesviruses, Poxviruses), single-stranded (+)sense DNA viruses (e.g. Parvoviruses), double-stranded RNA (e.g. Reoviruses) viruses, single-stranded (+)sense RNA (e.g. Picornaviruses, Togaviruses) viruses, or single-stranded (−)sense RNA viruses (e.g. Orthomyxoviruses, Rhabdoviruses). In some embodiments, the virus is a negative strand RNA virus such as those belonging to Bornaviridae, Filoviridae (e.g. Ebola virus, Marburg virus), Paramyxoviridae, Rhabdoviridae, Arenaviridae (e.g. Lassa virus), Bunyaviridae (e.g. Hantavirus), Orthomyxoviridae (e.g. Influenza viruses), and the like. In some embodiments, the virus is a double stranded DNA virus such as Myoviridae, Podoviridae, Siphoviridae, Ascoviridae, Adenoviridae, Asfarviridae, Baculoviridae, Coccolithoviridae, Corticoviridae, Fusellovaridae, Guttaviridae, Herpesviridae, Iridoviridae, Lipothrixviridae, Nimaviridae, Papillomaviridae, Phycodnaviridae, Plasmaviridae, Polyomaviridae, Poxyiridae (e.g. Cowpoxvirus, Monkeypox), Rudiviridae, Tectiviridae, and the like.

In some embodiments, Group VI (Baltimore classification system), reverse transcribing diploid single-stranded RNA viruses, and Group VII (Baltimore classification system), reverse transcribing circular double-stranded DNA viruses, are specifically excluded as the virus in the methods disclosed herein. In some embodiments, viruses belonging to the subfamily oncornavirinae, are specifically excluded as the virus in the methods disclosed herein. In particular, the claimed invention specifically excludes methods of preventing, inhibiting, or reducing the viral activity of an oncornavirus (a virus belonging to the subfamily oncornavirinae) on or in a cell or a subject or treating an infection in a cell or a subject caused by the oncornavirus which comprises administering to the cell or the subject an effective amount of one of the compounds specifically set forth in De Clercq & Dann (1980) J. Med. Chem. 23:787-795, which is herein incorporated by reference. As used herein, a compound set forth in De Clercq & Dann is referred to as an "excluded compound".

The activity of the compounds of the present invention may be measured by any of the methods available to those skilled in the art, including in vitro and in vivo assays. Examples of suitable assays for activity measurements are provided herein. Properties of the compounds of the present invention may be assessed, for example, by using one or more of the assays set out in the Examples below. Thus, one skilled in the art may readily screen, without undue experimentation, a given compound falling within the structural formulas described herein for antiviral activity. Other pharmacological methods may also be used to determine the efficacy of the compounds a subject suffering from a given disease or disorder. The compounds of the present invention may be used in combination with or as a substitution for treatments known in the art.

The therapeutically effective amounts of the compounds of the invention for treating the diseases or disorders described above in a subject can be determined in a variety of ways known to those of ordinary skill in the art, e.g. by administering various amounts of a particular compound to a subject afflicted with a particular condition and then determining the effect on the subject. Typically, therapeutically effective amounts of a compound of the present invention can be orally administered daily at a dosage of the active ingredient of 0.002 to 200 mg/kg of body weight.

Ordinarily, a dose of 0.01 to 10 mg/kg in divided doses one to four times a day, or in sustained release formulation will be effective in obtaining the desired pharmacological effect. It will be understood, however, that the specific dose levels for any particular subject will depend upon a variety of factors including the activity of the specific compound employed, the age, body weight, general health, sex, diet, time of administration, route of administration, and rate of excretion, drug combination and the severity of the particular disease.

Frequency of dosage may also vary depending on the compound used and the particular disease treated. It will also be appreciated that the effective dosage of the compound used for treatment may increase or decrease over the course of a particular treatment. Changes in dosage may result and become apparent by standard diagnostic assays known in the art. In some instances chronic administration may be required. The compounds of the present invention may be administered before, during, after, or a combination thereof exposure to bacteria.

As provided herein, an "effective amount" is intended to mean that amount of a compound that is sufficient to reduce, prevent or inhibit viral replication or infection as compared with a negative control. A "therapeutically effective amount" of a compound of the present invention, a prodrug, an active metabolite, or a salt thereof, is a quantity sufficient to, when administered to a subject, reduce, prevent or inhibit viral replication or infection. Also, as used herein, a "therapeutically effective amount" of a compound of the present invention is an amount which prevents, inhibits, suppresses, or reduces a given clinical condition in a subject as compared to a control. As defined herein, a therapeutically effective amount of a compound of the present invention may be readily determined by one of ordinary skill by routine methods known in the art.

The pharmaceutical formulations of the invention comprise at least one compound of the present invention and may be prepared in a unit-dosage form appropriate for the desired mode of administration. The pharmaceutical formulations of the present invention may be administered for therapy by any suitable route including oral, rectal, nasal, topical (including buccal and sublingual), dermal, mucosal, vaginal and parenteral (including subcutaneous, intramuscular, intravenous and intradermal). It will be appreciated that the preferred route will vary with the condition and age of the recipient, the nature of the condition to be treated, and the chosen compound of the present invention.

The compound can be administered alone, but will generally be administered as pharmaceutical formulations suitable for administration. Pharmaceutical formulations known in the art contemplated herein. Pharmaceutical formulations of this invention comprise a therapeutically effective amount of at least one compound of the present invention, and an inert, pharmaceutically or cosmetically acceptable carrier or diluent. As used herein the language "pharmaceutically acceptable carrier" or a "cosmetically acceptable carrier" is intended to include any and all solvents, dispersion media, coatings, antibacterial and antifungal agents, isotonic and absorption delaying agents, and the like, compatible with pharmaceutical or cosmetic administration. Except insofar as any conventional media or agent is incompatible with the active compound, use thereof in the formulation is contemplated. Descriptions of suitable pharmaceutically acceptable carriers, formulations, and factors involved in their selection, are found in a variety of readily available sources, e.g., Remington's Pharmaceutical Sciences, 17$^{th}$ ed., Mack Publishing Company, Easton, Pa., 1985, and Remington: The Science and Practice of Pharmacy, 21$^{st}$ ed., Lippincott Williams & Wilkins, 2005, which are incorporated herein by reference. which are incorporated herein by reference.

Supplementary active compounds can also be incorporated into the formulations. Supplementary active compounds include antibiotics, antiviral agents, antiprotozoal agents, antifungal agents, and antiproliferative agents known in the art, analgesics and other compounds commonly used to treat diseases and disorders associated with viral infection and toxic side effects of viral infection.

Antibiotics include penicillin, cloxacillin, dicloxacillin, methicillin, nafcillin, oxacillin, ampicillin, amoxicillin, bacampicillin, azlocillin, carbenicillin, mezlocillin, piperacillin, ticarcillin, azithromycin, clarithromycin, clindamycin, erythromycin, lincomycin, demeclocycline, doxycycline, minocycline, oxytetracycline, tetracycline, quinolone, cinoxacin, nalidixic acid, fluoroquinolone, ciprofloxacin, enoxacin, grepafloxacin, levofloxacin, lomefloxacin, norfloxacin, ofloxacin, sparfloxacin, trovafloxacin, bacitracin, colistin, polymyxin B, sulfonamide, trimethoprimsulfamethoxazole, co-amoxyclav, cephalothin, cefuroxime, ceftriaxone, vancomycin, gentamicin, amikacin, metronidazole, chloramphenicol, nitrofurantoin, co-trimoxazole, rifampicin, isoniazid, pyrazinamide, kirromycin, thiostrepton, micrococcin, fusidic acid, thiolactomycin, fosmidomycin, and the like.

Antiviral agents include abacavir, aciclovir, acyclovir, adefovir, amantadine, amprenavir, arbidol, atazanavir, atripla, brivudine, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, gardasil, ibacitabine, immunovir, idoxuridine, imiquimod, indinavir, inosine, lamivudine, lopinavir, loviride, maraviroc, nelfinavir, nevirapine, nexavir, oseltamivir, penciclovir, peramivir, pleconaril, podophyllotoxin, ribavirin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, zidovudine, and the like.

Antiprotozoal agents include chloroquine, doxycycline, mefloquine, metronidazole, eplornithine, furazolidone, hydroxychloroquine, iodoquinol, pentamidine, mebendazole, piperazine, halofantrine, primaquine, pyrimethamine sulfadoxine, doxycycline, clindamycin, quinine sulfate, quinidine gluconate, quinine dihydrochloride, hydroxychloroquine sulfate, proguanil, quinine, clindamycin, atovaquone, azithromycin, suramin, melarsoprol, eflornithine, nifurtimox, amphotericin B, sodium stibogluconate, pentamidine isethionate, trimethoprimsulfamethoxazole, pyrimethamine, sulfadiazine, and the like.

Antifungal agents include amphotericin B, fluconazole, itraconazole, ketoconazole, potassium iodide, flucytosine, and the like.

Antiproliferative agents such as altretamine, amifostine, anastrozole, arsenic trioxide, bexarotene, bleomycin, busulfan, capecitabine, carboplatin, carmustine, celecoxib, chlorambucil, cisplatin, cisplatin-epinephrine gel, cladribine, cytarabine liposomal, daunorubicin liposomal, daunorubicin daunomycin, dexrazoxane, docetaxel, doxorubicin, doxorubicin liposomal, epirubicin, estramustine, etoposide phosphate, etoposide VP-16, exemestane, fludarabine, fluorouracil 5-FU, fulvestrant, gemcitabine, gemtuzumabozogamicin, goserelin acetate, hydroxyurea, idarubicin, ifosfamide, imatinib mesylate, irinotecan, letrozole, leucovorin, levamisole, liposomal daunorubicin, melphalan L-PAM, mesna, methotrexate, methoxsalen, mitomycin C, mitoxantrone, paclitaxel, pamidronate, pegademase, pentostain, porfimer sodium, streptozocin, talc, tamoxifen, temozolamide, teniposide VM-26, topotecan, toremifene, tretinoin, ATRA, valrubicin, vinorelbine, zoledronate, steroids, and the like.

Medicaments for preventing, inhibiting, or reducing the viral activity of a virus on or in a cell or a subject or treating an infection in a cell or a subject caused by a virus comprising the compounds and compositions of the present invention and methods of manufacturing the medicaments are contemplated herein.

Toxicity and therapeutic efficacy of the compounds and compositions disclosed herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Additional Assays
1. Dose Response Assays—EBOV

To determine whether the compounds exhibit dose dependent antiviral activity against EBOV (GFP Zaire, see Towner et al. (2005) *Virology* 332(1):20-27, which is herein incorporated by reference), the following experiment was conducted. Vero E6 cells were plated on 96 well assay plates ($5 \times 10^4$ cells/well) in 100 μl cEMEM medium (EMEM (Invitrogen) with NEAA 41500-083 supplemented with 10% FBS (SH30071.03, HyClone) and 1% penicillin (P7794, Sigma Aldrich) and 1% streptomycin (S9137, Sigma Aldrich). The cells were cultured for 3 days at 37° C. in a humidified incubator (5% $CO_2$). Dilutions of the NSC 369723, NSC 294202, NSC 306365, NSC 300510, NSC 240893, and NSC 294206 were made at concentrations indicated on the X-axis of FIGS. 4A-4F in cEMEM medium under aseptic conditions. Media were removed from the wells of the 96 well plates and replaced by 100 μl of media containing the compounds at various concentrations including a control containing no compound. Each compound concentration was repeated in three wells (triplicate). The cells were then incubated again in the incubator at 37° C. for an additional 18 to 24 hours. After adding 50 μl of GFP-EBOV ($10^6$ infectious virus particles per ml) to each well, the cells were incubated at 37° C. for 40 to 48 hours. Then the media was aspirated and the assay plates with the cells were submerged in 4% formaldehyde in PBS buffer in plastic bags (one assay plate per bag) to inactivate the virus. The bags were sealed and incubated at room temperature for three days. Then, the formaldehyde solution was removed from the assay plates and replaced with 100 μl of PBS/well. The assay plates were then subjected to high throughput screening to measure the percent of the infected cells in each well. Specifically, the cells were imaged with a 10× objective lens on a Discovery-1 (Molecular Devices Corporation, Downingtown, Pa.) high content imager. The Discovery-1 was programmed to sequentially acquire images first with a DAPI filter set then with a GFP filter set for each of 9 image fields per well on a 96-well culture plate. Analysis was performed on MetaXpress software by modifying a "live dead" analysis module to count the total number of cells (based on the number of cell nuclei) and the number of infected cells (based on the number of nuclei associated with cytoplasmic GFP fluorescence). These numbers were used to calculate percent infection.

The average percent infected in each well was calculated from 9 individual spots read in each well. The percent infected data from the drug-treated wells were then normalized to the control by setting the percent infected cells in control wells (average of three wells) as 100 and calculating the efficiency of infection in drug-treated wells as percent of control infection according to the following equation:

$$\% \text{ of control infection} = \left(\frac{\% \text{ infected in experimental well}}{\text{mean }\% \text{ infected in control wells}}\right) \times 100$$

The data were then graphed by plotting % of control infection on Y-axis against drug concentration on the X-axis. At least three experiments were conducted for each drug and pooled (averaged) to generate summary graphs which are shown in FIGS. 4A-4F.

As shown in FIGS. 4A-4F, the compounds exhibit dose dependent antiviral activity toward EBOV. The compounds show $IC_{50}$'s in the low micromolar ranges except for NSC 306365 which shows a submicromolar $IC_{50}$.

2. Dose Response Assays—Rift Valley Fever Virus, Influenza Virus, Lassa Virus

The antiviral activities of compounds NSC 369723, NSC 294202, and NSC 306365 against Rift Valley Fever Virus (ZH501 strain, $2\times10^6$ pfu/ml), influenza virus (H1N1 A/Texas strain, $1\times10^5$ pfu/ml), and Lassa virus (Josiah strain, $7.9\times10^7$ pfu/ml) were examined in Vero E6 cells by measuring viral replication using plaque assays known in the art. Specifically, Vero E6 cells were plated on 96 well assay plates ($5\times10^4$ cells/well) in 100 µl cEMEM medium. The cells were cultured for 3 days at 37° C. in a humidified incubator (5% $CO_2$). Dilutions of the indicated compounds were made at concentrations of 0.25 µM, 0.5 µM, 1.0 µM, 2.0 µM, and 4.0 µM in cEMEM medium under aseptic conditions. Media were removed from the wells of the 96 well plates and replaced by 100 µl of media containing the compounds at various concentrations including a control containing no compound. Each compound concentration was repeated in three wells (triplicate). The cells were then incubated again in the incubator at 37° C. for an additional 18 to 24 hours. After adding 50 µl of a given virus ($10^6$ infectious virus particles per ml) to each a given well, the cells were incubated at 37° C. for an additional 1 hour. Then the excess viruses were removed from the cells, and the cells were washed two times with 200 µl/well of PBS. Fresh media containing the same compounds and at the same concentrations were added to the cells and the assay plates were incubated for 40 to 48 hours at 37° C. Then the supernatants were harvested and the content of infectious particles (replicated viruses) was measured in each sample was measured using plaque assays known in the art.

In particular, plaque assays for RVFV and Lassa virus were conducted as follows: In a 96-well plate, 225 µl cEMEM solution was added into the top row and 250 µl cEMEM was added in all other rows. Sample dilutions were made by adding 25 µl to the top well in each row. Using a multichannel pipettor, the samples were diluted 1:10 for 6 dilutions total down the plate. A positive control with a known titer was included in the assay as well as a negative no virus control. Two days prior to the assay start, 6-well plates were seeded with Vero 76 cells at $4\times10^5$ cells/well in cDMEM. The cDMEM from the Vero seeded 6-well plates was discarded into a container with Microchem Plus (0255, National Chemical Laboratories). Then starting with the lowest dilution of sample from the 96-well plate, 100 µl of sample was added in duplicate to the Vero 6-well plate. The 6-well plates were incubated at 37° C. with 5% $CO_2$ for one hour with rocking every 15 minutes to disperse the sample throughout the wells and prevent the cells from drying out. 2×EBME from Invitrogen (special catalog number 05-5068EF) supplemented with 10% FBS (SH30071.03, HyClone) and 2% penicillin (P7794, Sigma Aldrich) and 2% streptomycin (S9137, Sigma Aldrich) solution was warmed in a 42° C. water bath. A 1% SeaKem agarose (50014, Kaplan) mixture was made and heated in a microwave for about 7 to 10 minutes. This mixture was allowed to cool down to 42° C. in the water bath. A solution of equal parts of 2×EBME and 1% agarose was made before overlaying with 2 ml. The plates were returned to the incubator for about 6 to 8 days at 37° C. and 5% $CO_2$. After this incubation 2 ml overlay of 2×EBME and 1% agarose with 4% neutral red solution (Invitrogen). The plates were returned to the 37° C. and 5% $CO_2$ incubator for an additional day before the plaque assay was read.

For Influenza, the plaque assays were conducted as follows: Two days prior to the assay start, 6-well plates were seeded with MDCK cells at $4\times10^5$ cells/well in cRPMI (RPMI 1640, (11875, Invitrogen) supplemented with 10% heat inactivated FBS (SH30071.03, HyClone), 1% Non-essential Amino Acids (M7145, Sigma Aldrich), 1% Sodium Pyruvate (S8636, Sigma Aldrich) and 1% penicillin (P7794, Sigma Aldrich), 1% streptomycin (S9137, Sigma Aldrich)). In a 96 well plate, 225 µl cRPMI was added into the top row and 250 µl cRPMI was added into all subsequent rows. The sample dilutions were made by adding 25 µl to the top well in each row. Then using a multichannel pipettor, the samples were diluted 1:10 for 6 dilutions total down the plate. A positive control with a known titer was always included in the assay as well as a negative no virus control. The cRPMI media from the MDCK seeded 6-well plates was discarded into a container with Microchem Plus (0255, National Chemical Laboratories). Then starting with the lowest dilution of sample from the 96-well plate, 100 µl of sample was added in duplicate to the MDCK 6-well plates. The 6-well plates were incubated at 37° C. with 5% $CO_2$ humidity for one hour with rocking every 15 minutes to disperse the sample throughout the wells and prevent the cells from drying out. 2×EBME from Invitrogen (special catalog number 05-5068EF) supplemented with 10% FBS (SH30071.03, HyClone) and 2% penicillin (P7794, Sigma Aldrich) and 1% streptomycin (S9137, Sigma Aldrich) solution was warmed in a 42° C. water bath. A 1% SeaKem agarose (50014, Kaplan) mixture was made and heated in a microwave for about 7 to 10 minutes. This mixture was allowed to cool down to 42° C. in the water bath. A solution of equal parts of 2×EBME and 1% agarose was made before overlaying with 2 ml. The plates were returned to the incubator for about 6 to 8 days at 37° C. and 5% $CO_2$. After this incubation a 2 ml overlay of 2×EBME and 1% agarose with 4% neutral red solution (Invitrogen). The plates were returned to the 37° C. and 5% $CO_2$ incubator for an additional day before the plaque assay was read.

Figure 5A:
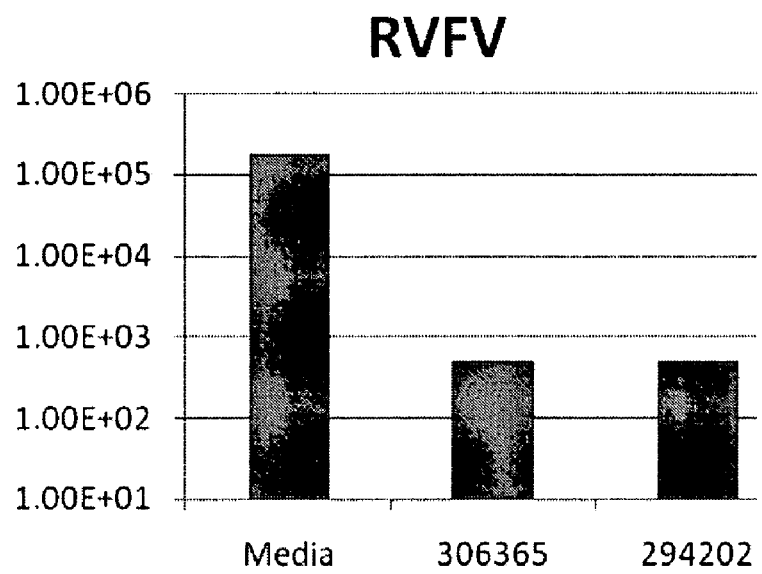
FIG. 5A shows that NSC 306365 at 4 µM and NSC 294202 at a concentration of 10 µM inhibit the replication of the ZH501 strain of Rift Valley fever virus (RVFV) in Vero-E6 cells.
Figure 5B:
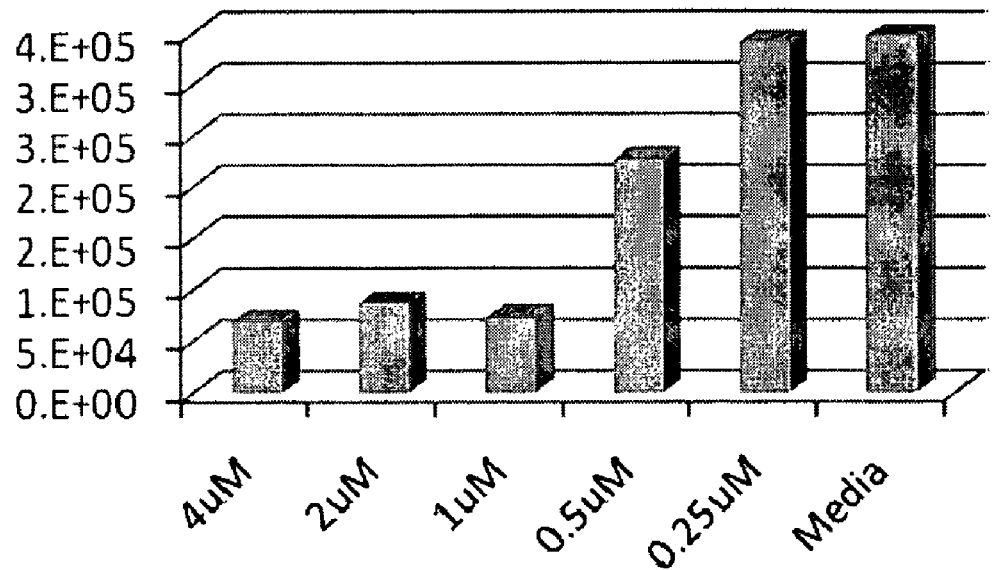
FIG. 5B shows that NSC 306365 exhibits dose dependent antiviral activity toward the ZH501 strain of Rift Valley fever virus (RVFV) in Vero-E6 cells.
Figure 5C:
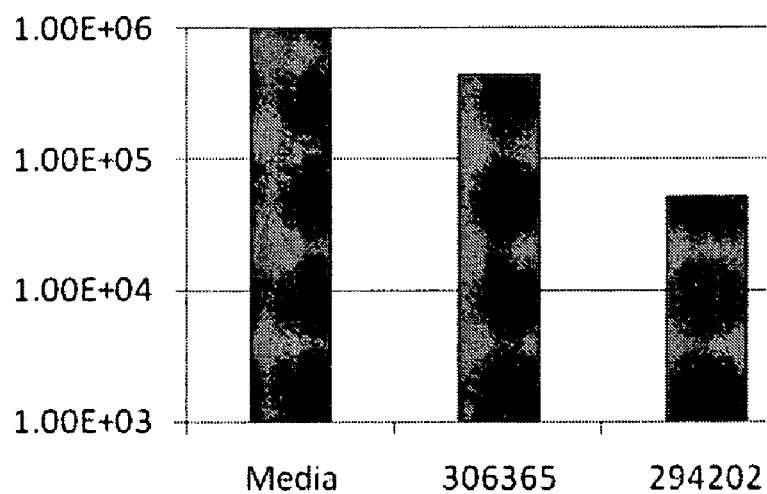
FIG. 5C shows that NSC 306365 at 4 µM and NSC 294202 at a concentration of 10 µM inhibit the replication of influenza virus (H1N1 A/Texas) in Vero-E6 cells.
Figures 5D, 6:
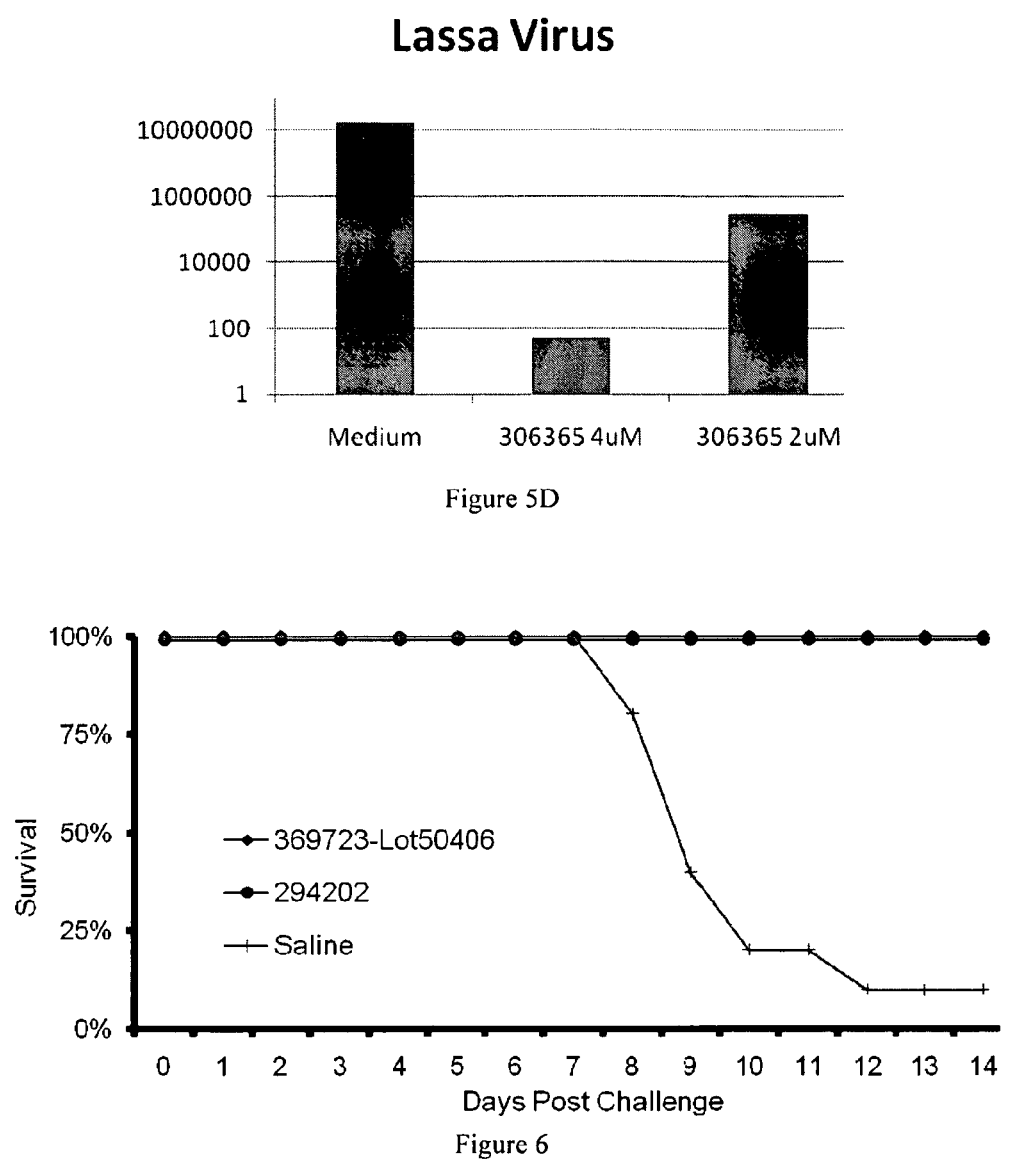

NSC 294202 and NSC 306365, but not NSC 369723, showed antiviral activity toward RVFV, LV, and influenza virus. FIGS. 5A-5D show the results of these experiments. FIG. 5A shows that NSC 306365 at 4 µM and NSC 294202 at 10 µM inhibit the replication of RVFV by over 100 fold. In FIG. 5B, the dose-dependent inhibition of RVFV by NSC 306365 is shown. FIG. 5C shows that NSC 306365 at 4 µM inhibits influenza virus replication by half log and NSC 294202 at 10 µM inhibits influenza replication by more than one log. FIG. 5D shows dose dependent inhibition of Lassa virus replication by NSC 306365, one log inhibition at 2 µM and over 3 log reduction at 4 µM.

3. In vivo Assays—EBOV

The antiviral activity of NSC 369723 and NSC 294202 against EBOV in vivo was examined. In these experiments, groups of 10 C57BL/6 mice were injected (i.p.) with 10 mg/kg of a given compound 1 hour before and on days 2 and 5 post challenge with 1000 pfu of mouse adapted EBOV (m-EBOV). See Bray et al. (1999) *J. Infect. Dis.* 179 (Suppl 1):S248-58, which is herein incorporated by reference. Control mice were injected with saline. All of the mice were injected (i.p.) with 1000 pfu virus each. Food and water were provided to the mice and the mice were monitored for at least 14 days post challenge. FIG. 6 shows the percent survival. As shown in FIG. 6, NSC 369723 and NSC 294202 provided 100% protection and 90% of the control mice died from infection.

Figure 7:
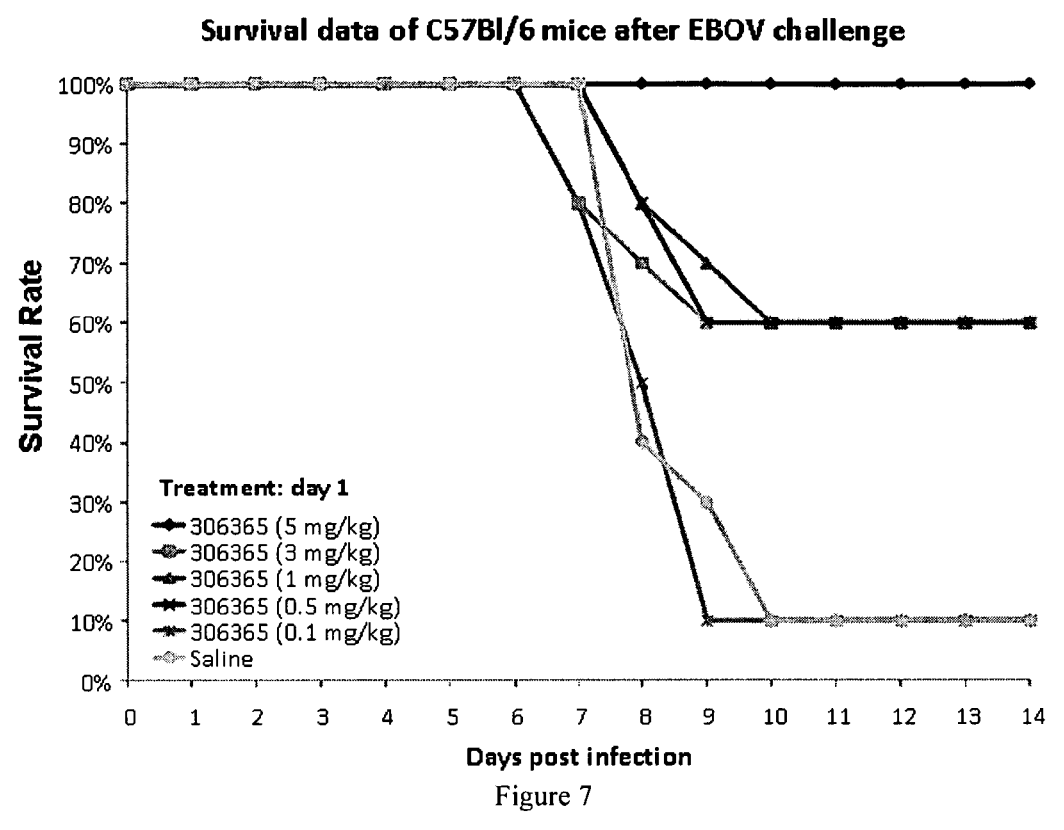

The antiviral activity of various doses of NSC 306365 post exposure was examined. In these experiments, groups of 10 C57BL/6 mice were challenged with 1000 pfu of m-EBOV each. After 24 hours post challenge, the mice of each group were injected (i.p.) with a given dose of NSC 306365. Food and water were provided to the mice and the mice were monitored for at least 14 days post challenge. As shown in FIG. 7, a 5 mg/kg dose of NSC 306365 conferred 100% protection against infection and doses as low as 0.5 mg/kg provided 60% protection.

4. In vivo Assays—Marburg Virus

Figure 8:
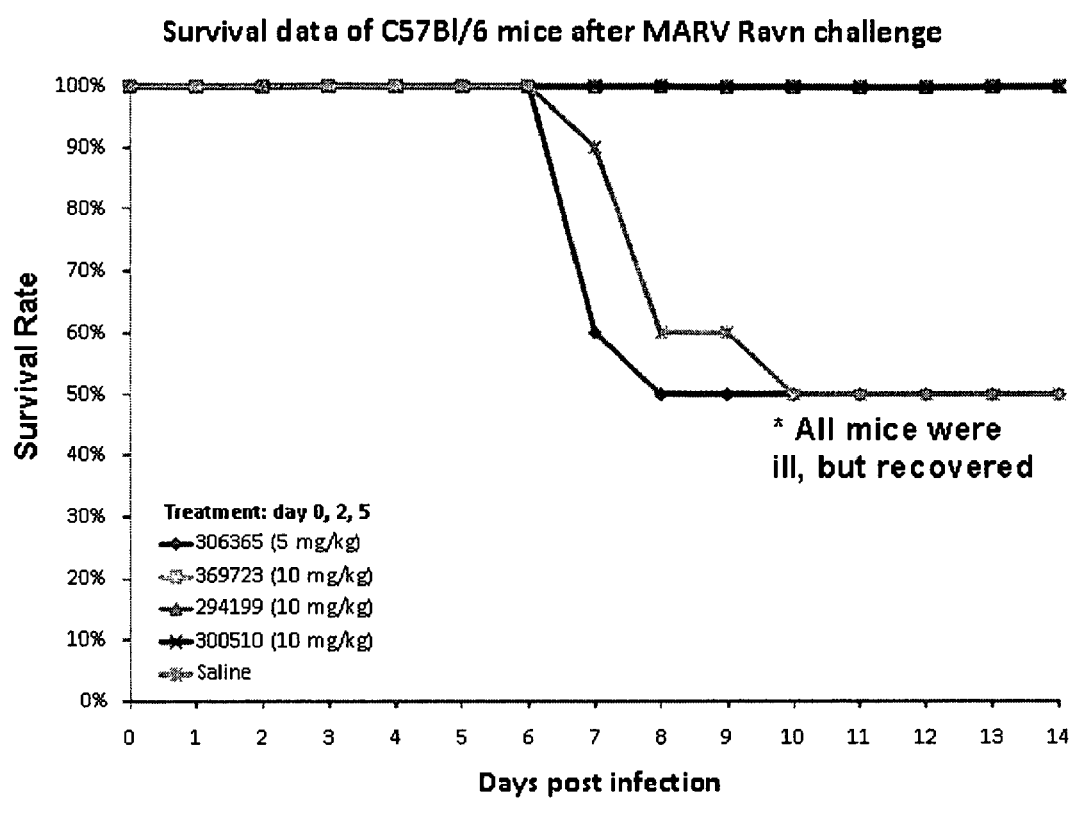
FIG. 8 shows that NSC 369723, NSC 294202, and NSC 300510 provided 100% protection against m-MARV in mice.

The antiviral activities of NSC 369723, NSC 294202, NSC 306365, and NSC 300510 were tested against Marburg virus infection in BALB/C mice. In these experiments, groups of 10 BALB/C mice were injected (i.p.) with 5 mg/kg of NSC 306365 or 10 mg/kg of NSC 369723, NSC 294202, or NSC 300510 1 hour before and on days 2 and 5 post challenge with 1000 pfu of mouse-adapted Marburg Ravn virus (R-MARV). See Warfield et al. (2007) *Virol. J.* 4:108, which is herein incorporated by reference and below. Control mice were injected with saline. All of the mice were injected (i.p.) with 1000 pfu virus each. Food and water were provided to the mice and the mice were monitored for at least 14 days post challenge. FIG. 8 shows the percent survival. As shown in FIG. 8, except for NSC 306365, NSC 369723, NSC 294202, and NSC 300510 provided 100% protection against m-MARV.

The mouse-adapted Marburg Ravn virus (R-MARV) was generated by serial passage of the virus in liver homogenates 25× through severe combined immunodeficient (scid) and then BALB/c mice. Serially passaging the livers from MARV-infected scid mice has been highly successful in reducing the time to death in scid mice from 50-70 days to 7-10 days following MARV-Ci67, -Musoke, or -Ravn challenge. See Warfield et al. (2007) *Virol. J.* 4:108, which is herein incorporated by reference. Further, sequential passages in BALB/c mice allowed the MARV to cause lethality in both BALB/c and C57BL/6 mice. Serial sampling studies to characterize the pathology of the mouse-adapted MARV-Ravn revealed that the mouse-adapted MARV model has many similar properties as the guinea pigs and primate MARV models. Infection of BALB/c mice with mouse-adapted MARV-Ravn caused uncontrolled viremia (>$10^6$ pfu/ml), extremely high viral titers in the liver, spleen, lymph node and other organs, profound lymphocytopenia and destruction of lymphocytes within the spleen and lymph nodes, and marked liver damage.

5. Pre- and Post-Exposure Efficacy

The pre- and post-exposure efficacy of NSC 300510 and post exposure efficacy of NSC 369723 and NSC 294199 were examined against EBOV infection in mice. In these experiments, Group 1 of 10 BALB/C mice were injected (i.p.) with 10 mg/kg of a NSC 300510 1 hour before challenge with 1000 pfu of mouse adapted EBOV (m-EBOV). The remaining groups, Groups 2-5, of mice were injected with saline. On day 1 after challenge, Group 1 was injected with saline, group 2 with NSC 300510, group 3 with NSC 294199, group 4 with NSC 369723, and group 5 with saline. On day 2 after injection, group 1 was injected with NSC 300510. On day 5 after injection all the groups were injected again with the same compounds as administered before. Thus the first group received NSC 300510 on days 0, 2, 5 (pre and post exposure), and the groups 2-4 received the respective compounds only post exposure (days 1 and 5 after challenge).

Figure 9:
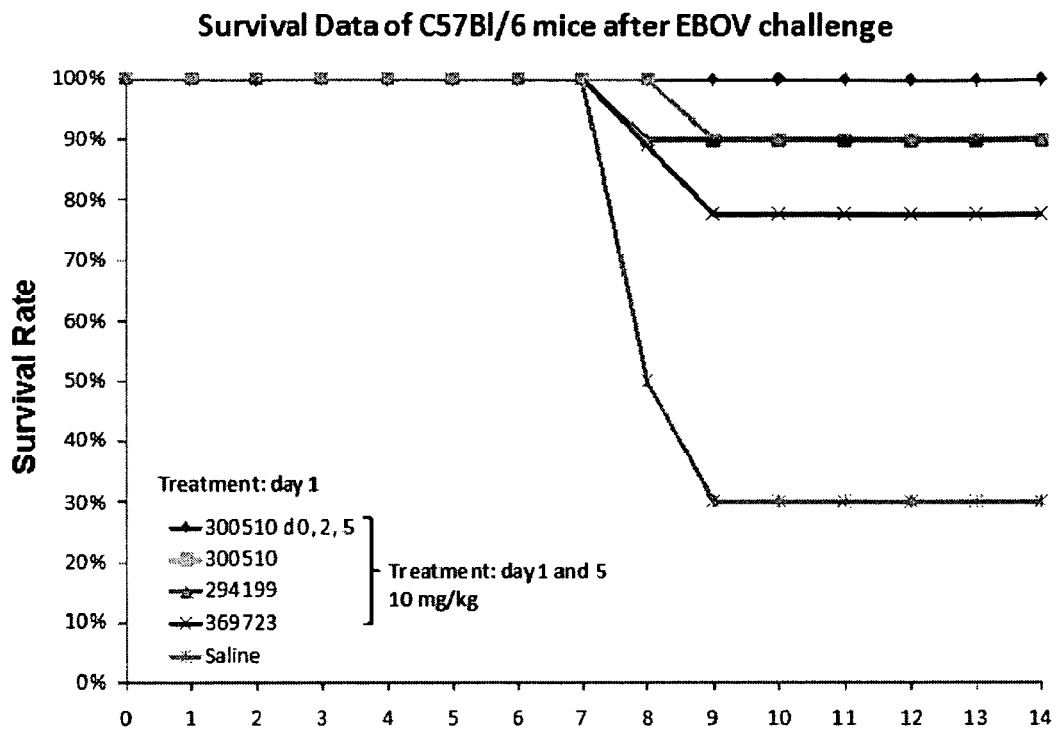
FIG. 9 shows that two injections of NSC300510, NSC294199, and NSC369723 on days 1 and 5 after infection of C57BL/6 mice with EBOV (1000 pfu) confers protection against death.

Food and water were provided to the mice and the mice were monitored for at least 14 days post challenge. Percent survival on each day was calculated and plotted. As shown in FIG. 9, when administered on days 0, 2, and 5, NSC 300510 protected 100% of mice. When the treatment was delayed to 24 hours after infection, 90% of treated mice survived. In the control group, all became ill and only 30% survival was observed.

6. Cellular Action

A. To determine if pre-treatment of cells with NSC 369723 increases their antiviral activity, i.e. induces an antiviral state in the cells, the following experiment was conducted. Vero E6 cells were plated on 96 well assay plates ($5\times10^4$ cells/well) in 100 µl cEMEM medium. The cells were cultured for 3 days at 37° C. in a humidified incubator (5% $CO_2$). Media were removed from the wells of the 96 well plates and replaced by 100 µl of media containing 10 µM NSC 369723 including a control containing no compound. Each compound concentration was repeated in three wells (triplicate). The cells were then incubated again in the incubator at 37° C. for an additional 18 to 24 hours. Three wells received medium containing no drug as control. The experimental wells were as follows:

Wells 1-3: medium only
Wells 4-6: 10 µM 369723 in cEMEM medium
Wells 7-9: medium only Then the media in wells 1-9 was removed and cells were washed with 200 µl PBS three times and 100 µl fresh medium without compound was added to wells 1-6. 100 µl of 10 µM NSC 369723 was added to the wells 7-9. After adding 50 µl of GFP-EBOV ($10^6$ infectious virus particles per ml) to each well, the cells were incubated at 37° C. for 1 hour. Then the media in wells 1-9 was removed and the cells were washed with 200 µl PBS three times. 100 µl fresh medium without compound was added to wells 1-6. 100 µl of 10 µM NSC 369723 was added to the wells 7-9. The cells were incubated at 37° C. for an additional 40 to 48 hours. Thus, the cells in wells 1-3 did not receive compound at any time, cells in wells 4-6 were treated with compound only before infection, and the cells in wells 7-9 were not pretreated with the compound, but treated during and after infection.

Then the media was aspirated and the assay plates with the cells were submerged in 4% formaldehyde in PBS buffer in plastic bags (one assay plate per bag) to inactivate the virus. The bags were sealed and incubated at room temperature for three days. Then, the formaldehyde solution was removed from the assay plates and replaced with 100 µl of PBS/well. The assay plates were then subjected to high throughput screening as described above to measure the percent of the infected cells in each well. The average percent infected in each well was calculated from 9 individual spots read in each well. The percent infected data from the drug-treated wells were then normalized to the control by setting the percent infected cells in control wells (average of three wells) as 100 and calculating the efficiency of infection in drug-treated wells as percent of control infection according to the following equation:

$$\% \text{ of control infection} = \left(\frac{\% \text{ infected in experimental well}}{\text{mean } \% \text{ infected in control wells}}\right) \times 100$$

Figure 10A:
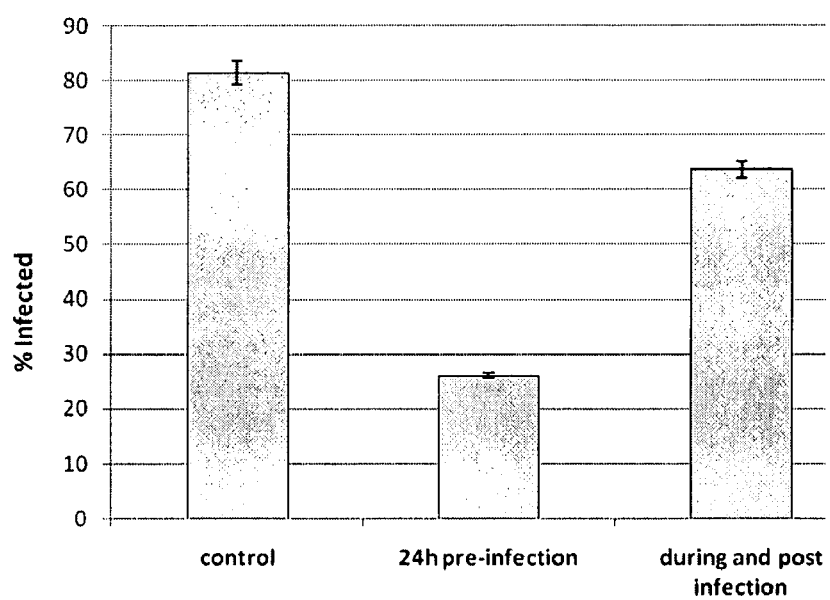
FIG. 10A shows that cells pretreated with NSC 369723 for 24 hours (and its removal during and after infection) is more effective than treatment during and after infection.

The data were then graphed by plotting % of control infection on Y-axis against compound concentration on the X-axis and is shown in FIG. 10A.

B. To determine if pre-treatment of cells with the NSC 369723 increases their antiviral activity, i.e. induces an antiviral state in the cells, the following experiment was conducted. Vero E6 cells were plated on 96 well assay plates ($5 \times 10^4$ cells/well) in 100 µl cEMEM medium. The cells were cultured for 3 days at 37° C. in a humidified incubator (5% $CO_2$). Three sets of 24 wells were labeled on the plated as:

1st set: wells 1-24
2nd set: wells 25-48
3rd set: wells 49-72

Media were removed from the wells and replaced by 100 µl of media containing NSC 369723 at various concentrations: 0, 0.31, 0.63, 1.25, 2.50, 5.00, 10.00, and 20.00 µM in the following manner: The first three wells of the first set received medium only (0 concentration), followed by the next 3 wells of the first set receiving 0.31 µM, and this was continued in the same manner until the 8th three wells of the first set received the 20 µM compound dilution. All the wells in the second and third set only received medium. The cells were then incubated again in the incubator at 37° C. for an additional 24 hours.

Then the media on the second and third sets were removed and replaced with compound dilutions in the same manner as described above for the 1st set. Cells were then incubated again in the incubator at 37° C. for additional 24 hours. Then the media on 1st and 2nd sets were removed. The media on the first two sets was replaced with compound free medium. After adding 50 µl of GFP-EBOV ($10^6$ infectious virus particles per ml) to each well, the cells were incubated at 37° C. for 1 hour. Then the media in wells of all three sets was removed and cells were washed with 200 µl PBS three times. Medium without compound as added to the first and second set wells. For the third set of wells, the compound concentrations as described above were added in the same manner. In this way the following treatment profile was achieved:

$1^{st}$ Set: Received compound dilutions 48 hour before infection but not during or after infection.
$2^{nd}$ Set: Received compound dilutions 24 hour before infection but not during or after infection.
$3^{rd}$ Set: Received compound dilutions 24 hour before infection as well as during and after infection.

The cells were incubated for an additional 40 to 48 hours. Then the media was aspirated and the assay plates with the cells were submerged in 10% buffered formalin (VT450D, ValTech Diagnostics, Pittsburg, Pa.) in plastic bags (one assay plate per bag) to inactivate the virus. The bags were sealed and incubated at room temperature for three days. Then, the formaldehyde solution was removed from the assay plates and replaced with 100 µl of PBS/well. The assay plates were then subjected to high throughput screening as described above to measure the percent of the infected cells in each well. The average percent infected in each well was calculated from 9 individual spots read in each well. The percent infected data from the drug-treated wells were then normalized to the control by setting the percent infected cells in control wells (average of three wells) as 100 and calculating the efficiency of infection in drug-treated wells as percent of control infection according to the following equation:

$$\% \text{ of control infection} = \left(\frac{\% \text{ infected in experimental well}}{\text{mean } \% \text{ infected in control wells}}\right) \times 100$$

Figure 10B:
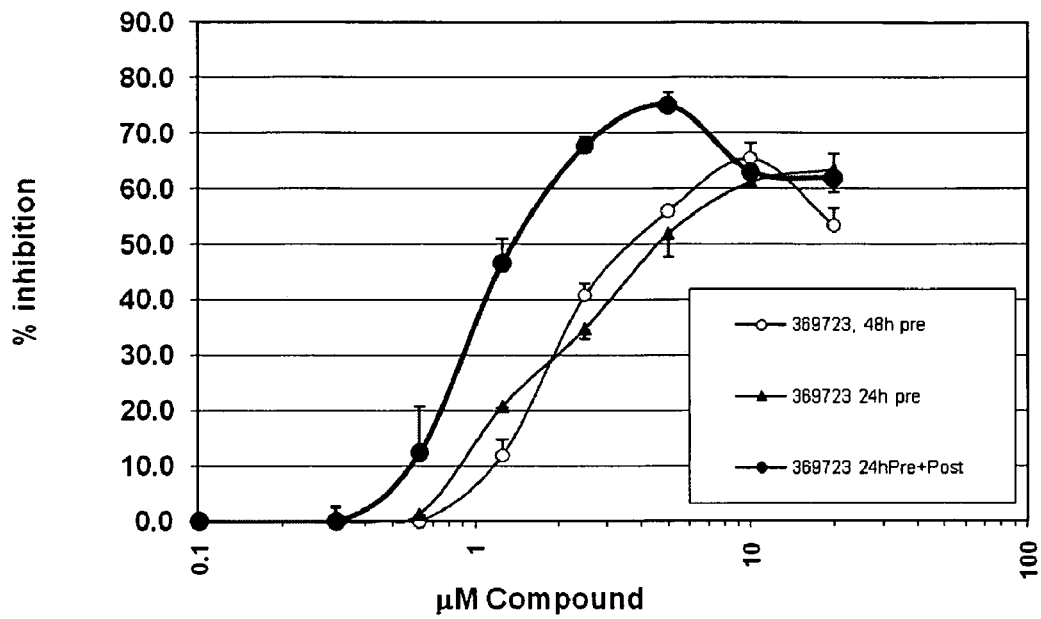
FIG. 10B shows the % inhibition of infection determined after 48 hours in cells that were treated with NSC 369723 for 24 hours or 48 hours and washed away before infection or kept in culture during infection.

The data were then graphed by plotting % of inhibition on Y-axis against compound concentration on the X-axis and is shown in FIG. 10B.

C. To determine if pre-treatment of the virus (not cells) with NSC 369723 and or NSC 294202 results in antiviral activity, the following experiment was conducted. Because of the carry-over of the compounds to the cells there is some compound also in the culture and those concentrations are indicated on the X axis of FIG. 10C in red. The serial dilution results in decreasing multiplicity of infection (MOI). The resulting MOIs are indicate on the X axis of FIG. 10C in black. Vero E6 cells were plated on 96 well assay plates ($5 \times 10^4$ cells/well) in 100 µl cEMEM medium. The cells were cultured for 3 days at 37° C. in a humidified incubator (5% $CO_2$).

Figure 10C:
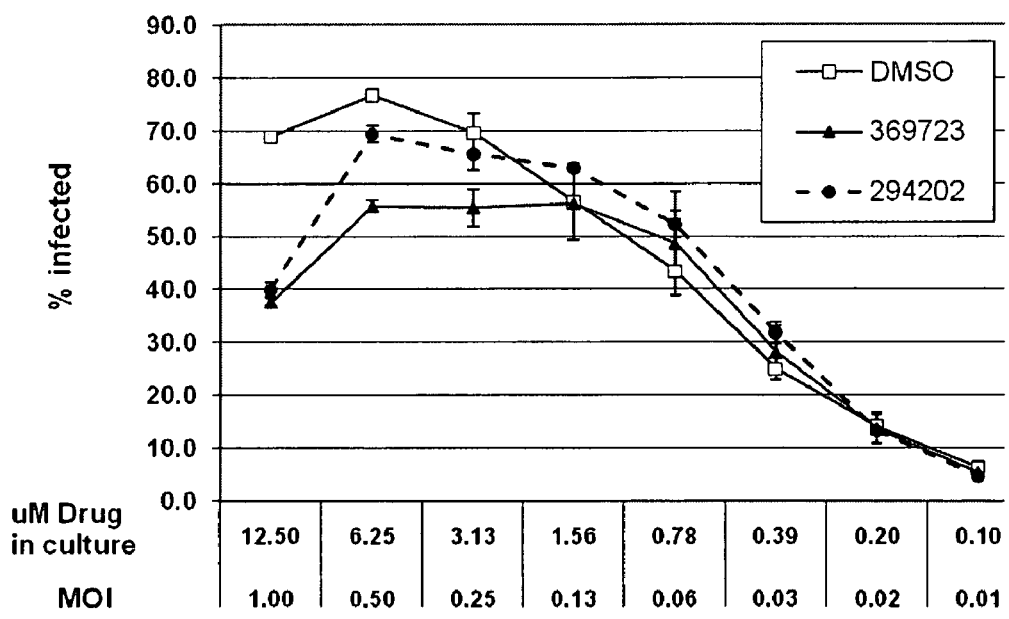
FIG. 10C shows the % inhibition of infection determined after 48 hours in cells after challenge with virus that was pre-incubated with NSC 369723 or NSC 294202. The resulting MOI and the concentration of the drug that was carried over to the cells are shown.

100 µl of a stock of GFP-EBOV containing $10^8$ pfu/ml was incubated for 30 minutes at room temperature with 100 µM concentration of either NSC 369723 (Tube 1) or NSC 294202 (Tube 2) or dimethyl sulfoxide (DMSO; the solvent of the drugs) as control (Tube 3). After the incubation the treated virus in each tube was diluted in medium to a total volume of 200 µ individual spots read in each well. The data were then graphed by plotting % infected on Y-axis against carried over compound concentration and the respective resulting MOI on the X-axis and are shown in FIG. 10C. As shown in FIG. 10C, except for the first two drug concentrations (12.5 and 6.25 µM) where inhibition was expected as result of carry over, the compound curves overlap with the DMSO curve, thereby suggesting that pretreatment of the virus with the compounds had no effect on activity of the virus.

Other Viruses

1. Cowpox Virus

Figure 11:
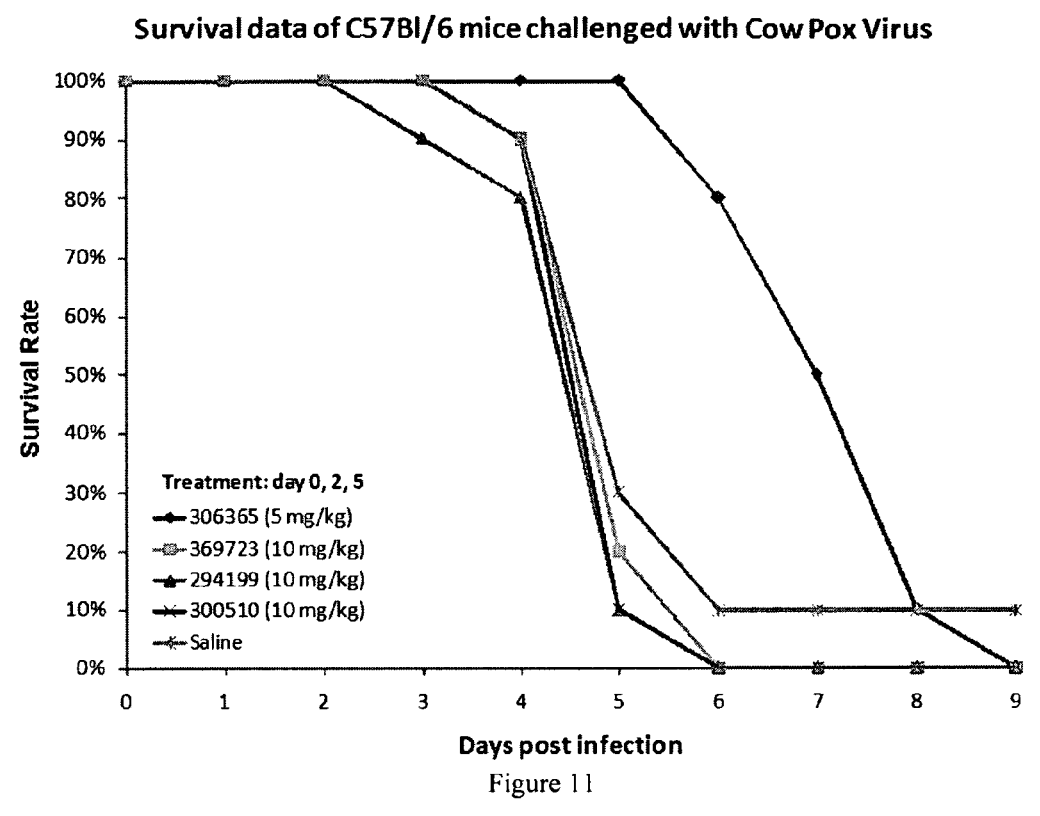

The effect of the compounds of the present invention on poxvirus was examined in a mouse model of cowpox virus ("CPXV", egfpCPV virus). See Goff et al. (2007) *Virus Research* 128(1-2):88-98, which is herein incorporated by reference. In these experiments, BALB/c mice were injected (i.p.) with 5 mg/kg NSC 306265, or 10 mg/kg for NSC 369723, NSC 294199, or NSC 300510 on days 0, 2, 5 and challenged with $5 \times 10^7$ pfu i.p. of CPXV on day 0. Food and water were provided to the mice and the mice were monitored for at least 14 days post challenge. Percent survival on each day was calculated and plotted and is shown in FIG. 11. In this experiment, NSC 306365 provided an increase in the mean time to death.

2. Monkeypox Virus

Compounds that showed activity toward MPXV-GFP in the initial screening were also tested for inhibitory activity toward a recombinant monkeypox virus expressing GFP (MPXV-GFP). The monkeypox virus (Zaire strain) expressing GFP was made in the same manner as described in Goff et al. (2007) *Virus Res.* 128(1-2):88-98, Epub 2007 May 23, which is herein incorporated by reference. Vero E6 cells ($5 \times 10^4$ cells/well) were grown to monolayers in 96 well plates to which 20 µM of each compound was added to a given well. Subsequently (within about 1 to about 2 hours), $5 \times 10^4$ of MPXV-GFP was added to the cells and then the cells were incubated at 37° C. for 48 hours. Then the cells were fixed for 3 days in formalin, the nuclei were stained with Hoechst Dye. To quantify the percent infection and the intensity of green fluorescent light from GFP expression, a Discovery-1 high content screening device (Molecular Devices Corp., Downingtown, Pa.) was applied for 9 regions per well. Percent infection in the treated cells was compared with untreated cells (controls) on the same 96 well plates. The activity of these compounds is provided in Table 1.

Although the experiments exemplified herein are based on mice and mouse cells and tissues, other subjects, such as humans, non-human primates, and other animals, and cells and tissues thereof are contemplated herein.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A method of inhibiting or reducing the viral activity of a virus belonging to the Filoviridae or Poxviridae family on or in a cell or a subject which comprises administering to the cell or the subject an effective amount of a compound having the following structural formula

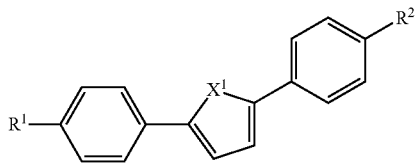

X$^1$ is;
R$^1$, R$^2$ and R$^7$ are each independently hydrogen, amino, amine with stabilized carbocations, carboxyl, optionally substituted alkyl, alkenyl, alkynyl, cycloalkyl, heterocycloalkyl, aryl, heteroaryl, alkoxy, aryoxy, cycloalkoxy, heteroaryloxy, alkoxycarbonyl, alkylamino, carbamoyl, alkylaminocarbonyl, alkylsulfhydryl, alkylhydroxymate, or an amide possessing an alkyl substituent; and
R$^8$ is hydrogen, OH, a halogen, or an optionally substituted alkyl.

2. The method of claim 1, wherein the compound is NSC300510.

3. The method of claim 1, wherein the virus is a negative strand RNA virus or a double stranded DNA virus.

4. The method of claim 1, wherein the virus is an Ebolavirus, a Marburgvirus, or an Orthopoxvirus.

5. The method of claim 1, wherein the virus is Zaire Ebolavirus, Reston Ebolavirus, Sudan Ebolavirus, Ivory Coast Ebolavirus, Bundibugyo Ebolavirus, Marburgvirus, Cowpox virus, or Monkeypox virus.

6. A method of treating an infection in a cell or a subject caused by a virus belonging to the Filoviridae or Poxviridae family which comprises administering to the cell or the subject an effective amount of a compound having the following structural formula

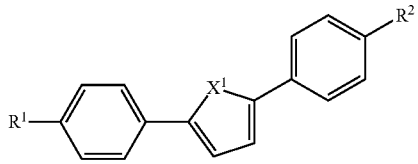

X$^1$ is;
R$^1$, R$^2$ and R$^7$ are each independently hydrogen, amino, amine with stabilized carbocations, carboxyl, optionally substituted alkyl, alkenyl, alkynyl, cycloalkyl, heterocycloalkyl, aryl, heteroaryl, alkoxy, aryoxy, cycloalkoxy, heteroaryloxy, alkoxycarbonyl, alkylamino, carbamoyl, alkylaminocarbonyl, alkylsulfhydryl, alkylhydroxymate, or an amide possessing an alkyl substituent; and
R$^8$ is hydrogen, OH, a halogen, or an optionally substituted alkyl.

7. The method of claim 6, wherein the compound is NSC 300510.

8. The method of claim 6, wherein the virus is a negative strand RNA virus or a double stranded DNA virus.

9. The method of claim 6, wherein the virus is an Ebolavirus, a Marburgvirus, or an Orthopoxvirus.

10. The method of claim 6, wherein the virus is Zaire Ebolavirus, Reston Ebolavirus, Sudan Ebolavirus, Ivory Coast Ebolavirus, Bundibugyo Ebolavirus, Marburgvirus, Cowpox virus, or Monkeypox virus.

* * * * *